US010786677B2

(12) United States Patent
Parramon et al.

(10) Patent No.: US 10,786,677 B2
(45) Date of Patent: Sep. 29, 2020

(54) LOCALLY-POLARIZED AND GLOBALLY UNPOLARIZED NEUROMODULATION SYSTEM AND METHOD

(71) Applicant: Boston Scientific Neuromodulation Corporation, Valencia, CA (US)

(72) Inventors: Jordi Parramon, Valencia, CA (US); Tianhe Zhang, Studio City, CA (US); Rafael Carbunaru, Valley Village, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 163 days.

(21) Appl. No.: 15/788,528

(22) Filed: Oct. 19, 2017

(65) Prior Publication Data
US 2018/0110992 A1 Apr. 26, 2018

Related U.S. Application Data

(60) Provisional application No. 62/411,444, filed on Oct. 21, 2016.

(51) Int. Cl.
*A61N 1/36* (2006.01)
*A61N 1/05* (2006.01)
*A61N 1/372* (2006.01)

(52) U.S. Cl.
CPC ........ *A61N 1/36189* (2013.01); *A61N 1/0551* (2013.01); *A61N 1/36062* (2017.08);
(Continued)

(58) Field of Classification Search
CPC ............ A61N 1/36189; A61N 1/36146; A61N 1/36164; A61N 1/36071; A61N 1/36062; A61N 1/0551
See application file for complete search history.

(56) References Cited

U.S. PATENT DOCUMENTS 8,412,345 B2 4/2013 Moffitt
8,909,350 B2 12/2014 Lee
(Continued)

FOREIGN PATENT DOCUMENTS

WO WO-2018075791 A1 4/2018

OTHER PUBLICATIONS

Arle, Jeffrey E., et al., "High-Frequency Stimulation of Dorsal Column Axons: Potential Underlying Mechanism of Paresthesia-Free Neuropathic Pain Relief", Neuromodulation 19: 385-397 (2016).
(Continued)

*Primary Examiner* — Alyssa M Alter
(74) *Attorney, Agent, or Firm* — Schwegman Lundberg & Woessner, P.A.

(57) ABSTRACT

Multi-phasic fields are produced at a neuromodulation site using electrodes. A first phase is directed at a target region such that a first-polarity electrical charge is injected to the target region, and a second phase is directed at portions of the neuromodulation site other than the target region, such that a second-polarity electrical charge opposite the first-polarity electrical charge is injected to those portions of the neuromodulation site to essentially neutralize the first-polarity charge injected at the neuromodulation site while maintaining at least a portion of the first-polarity charge at the target region. In some embodiments, each anode used to produce the first phase is used as a cathode to produce the second phase, and each cathode used to produce the first phase is used as an anode to produce the second phase, and the quantity of charge injected by each electrode in both phases is essentially zero.

20 Claims, 13 Drawing Sheets

(52) U.S. Cl.
CPC ..... *A61N 1/36071* (2013.01); *A61N 1/36146* (2013.01); *A61N 1/36164* (2013.01); *A61N 1/36167* (2013.01); *A61N 1/37247* (2013.01)

(56) References Cited

U.S. PATENT DOCUMENTS

| | | |
|---|---|---|
| 2004/0127953 A1 | 7/2004 | Kilgore et al. |
| 2010/0331925 A1 | 12/2010 | Peterson |
| 2013/0238059 A1 | 9/2013 | York et al. |
| 2014/0277259 A1 | 9/2014 | Rosenberg et al. |
| 2014/0296942 A1 | 10/2014 | Moffitt et al. |

OTHER PUBLICATIONS

"European Application Serial No. 17791901.6, Response to Communication Pursuant to Rules 161 and 162 filed Dec. 19, 2019", 11 pgs.

"International Application Serial No. PCT/US2017/057426, International Preliminary Report on Patentability dated May 2, 2019", 9 pgs.

"International Application Serial No. PCT/US2017/057426, International Search Report dated Jan. 4, 2018", 7 pgs.

"International Application Serial No. PCT/US2017/057426, Written Opinion dated Jan. 4, 2018", 7 pgs.

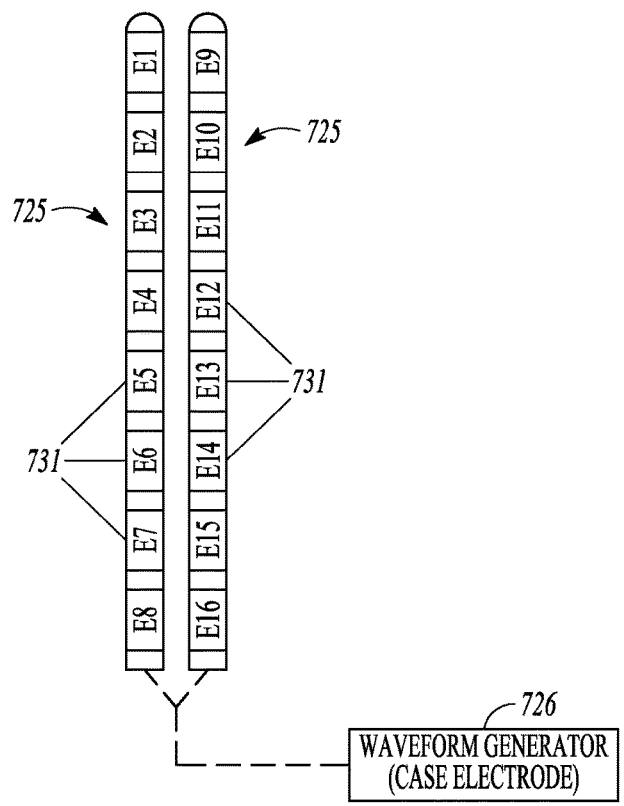
FIG. 7
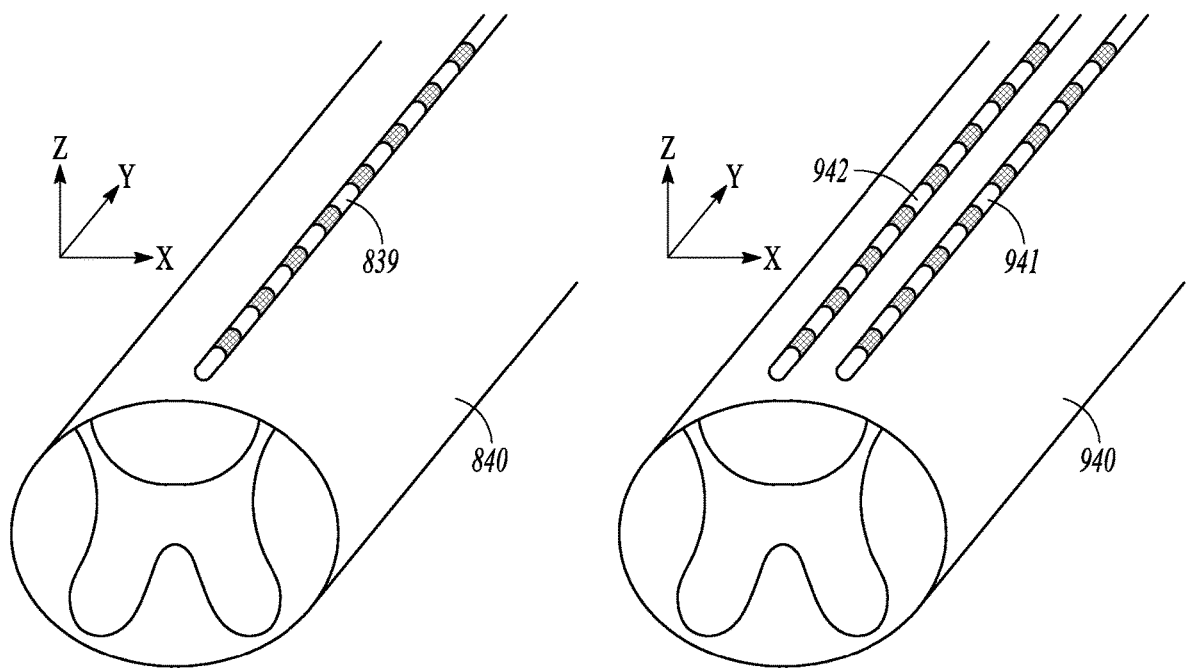
FIG. 8
FIG. 9

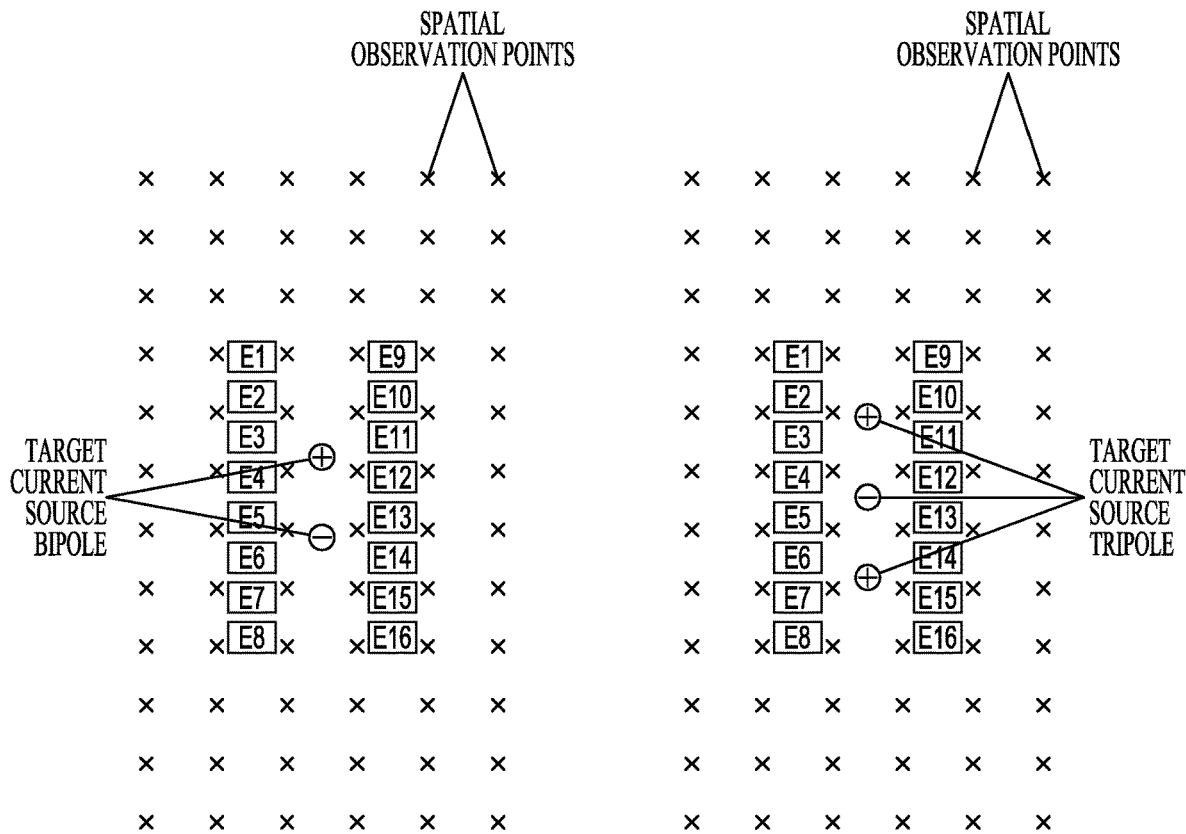
*FIG. 18A*  *FIG. 18B*
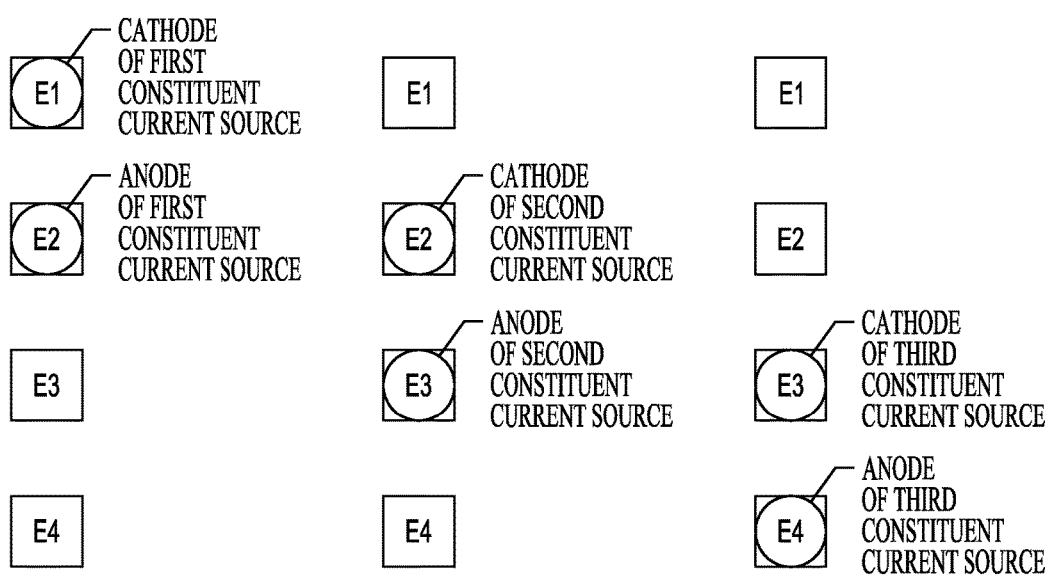
*FIG. 19A*  *FIG. 19B*  *FIG. 19C*

LOCALLY-POLARIZED AND GLOBALLY UNPOLARIZED NEUROMODULATION SYSTEM AND METHOD

CLAIM OF PRIORITY

This application claims the benefit of priority under 35 U.S.C. § 119(e) of U.S. Provisional Patent Application Ser. No. 62/411,444, filed on Oct. 21, 2016, which is herein incorporated by reference in its entirety.

TECHNICAL FIELD

This document relates generally to medical devices, and more particularly, to systems, devices and methods for delivering neuromodulation.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Conventional SCS delivers electrical pulses to the dorsal column fibers in the dorsal aspect of the spinal cord, which in turn activate a set of inhibitory neurons in the dorsal horn, thereby masking the transmission of pain signals from the periphery of the body to the brain. One of the underlying theories behind the inhibitory mechanisms of action is that it is modulation of the pre-synaptic terminals of the dorsal horn that produces the desired therapeutic effect. It has also been hypothesized that modulation of elements of the dorsal column tends to cause a paresthesia effect, which patients may perceive as discomfort in some cases. Accordingly, it would be desirable for a neuromodulation device to be able to modulate the pre-synaptic terminals without causing undue paresthesia due to stimulation of other elements of the dorsal horn or dorsal column.

The pre-synaptic terminals may be suitably modulated by charging them to a certain extent, such that the membranes are hyperpolarized, or partially depolarized, but not necessarily activated. This type of neuromodulation may be achieved using relatively low-amplitude, long-duration pulses, as compared with other types of neuromodulation waveforms.

However, application of a net-polarized electrotherapy waveform having a direct-current (DC) component may be harmful to the patient, and causes galvanic corrosion of electrodes, making it impractical for electrode-based neuromodulation devices. Accordingly, conventional devices tend to use multi-phasic waveforms in which the polarity is reversed so as to produce no net DC component. This approach hampers neuromodulation techniques that involve maintaining a nonzero net charge in targeted tissue. As another approach, high-frequency spinal cord stimulation has been proposed, which takes advantage of rectification properties of target tissue to result in a net DC component in the administered electrotherapy. There may be other electrotherapy applications where administering a net charge to the target tissue may be desired, but poses associated challenges such as those discussed above, or other challenges. Accordingly, a practical solution is needed.

SUMMARY

The following examples illustrate various aspects of the embodiments described herein.

Example 1 is an apparatus for a neuromodulation system, comprising: means for producing multi-phasic fields at a neuromodulation site using an electrode arrangement; and means for coordinating production of the multi-phasic fields, wherein the multi-phasic fields include: a first phase to be directed at a target region of the neuromodulation site, such that a first-polarity electrical charge is injected to the target region; and a second phase to be directed at portions of the neuromodulation site other than the target region, such that a second-polarity electrical charge opposite the first-polarity electrical charge is injected to those portions of the neuromodulation site to essentially neutralize the first-polarity charge injected at the neuromodulation site while maintaining at least a portion of the first-polarity charge at the target region.

In Example 2, the subject matter of Example 1 optionally includes the second phase being subsequent to the first phase.

In Example 3, the subject matter of any one or more of Examples 1-2 optionally includes the first-polarity electrical charge injected to the target region in the first phase produces a bioelectric neuromodulation effect in the target region, and the second-polarity electrical charge injected to the neuromodulation site avoids counteracting the bioelectric neuromodulation effect.

In Example 4, the subject matter of Example 3 optionally includes the bioelectric neuromodulation effect including one of: hyperpolarization, or partial depolarization, of neural tissue of the target region to produce a pain-suppressive therapeutic effect.

In Example 5, the subject matter of any one or more of Examples 3-4 optionally includes, the bioelectric neuromodulation effect including a sub-perception polarization of neural tissue of the target region to produce a pain-suppressive therapeutic effect.

In Example 6, the subject matter of any one or more of Examples 1-5 optionally includes the first-polarity electrical charge injected to the target region in the first phase produces a first bioelectric neuromodulation effect in the target region, and the second-polarity electrical charge injected to the neuromodulation site causes a second bioelectric neuromodulation effect outside of the target region.

In Example 7, the subject matter of any one or more of Examples 1-6 optionally includes each of the first phase and the second phase having a corresponding field shape that is produced by fractional energization of a plurality of individual electrodes.

In Example 8, the subject matter of any one or more of Examples 1-7 optionally includes the first phase being directed primarily the target region including pre-synaptic terminals of the dorsal horn or of the afferent nerve fibers, and the second phase being directed primarily at dorsal structures.

In Example 9, the subject matter of any one or more of Examples 1-8 optionally includes the first phase and the second phase each being produced using a plurality of anodes and a plurality of cathodes of the electrode arrangement, and wherein each anode used to produce the first phase is used as a cathode to produce the second phase, and each cathode used to produce the first phase is used as an anode to produce the second phase.

In Example 10, the subject matter of Example 9 optionally includes a first quantity of charge of the first polarity is injected to the neuromodulation site through each one of the individual electrodes during the first phase and a second quantity of charge of the second polarity injected to the neuromodulation site during the second phase, wherein the first quantity equals the second quantity.

In Example 11, the subject matter of any one or more of Examples 1-10 optionally includes, wherein the first phase and the second phase having different field shapes and different waveforms.

In Example 12, the subject matter of any one or more of Examples 1-11 optionally includes, the first phase including a sub-threshold pulse of between 10 microseconds and 1000 microseconds, and wherein the second phase includes a plurality of pulses, each of which is shorter than 10 microseconds.

Example 13 is a method for operating a neuromodulation system to produce multi-phasic fields at a neuromodulation site using a set of electrodes of an electrode arrangement, the method comprising: applying a first phase of the multi-phasic fields to be directed at a target region of the neuromodulation site, such that a first-polarity electrical charge is injected to the target region; and applying a second phase of the multi-phasic fields to be directed at portions of the neuromodulation site other than the target region, such that a second-polarity electrical charge opposite the first-polarity electrical charge is injected to those portions of the neuromodulation site; wherein the first phase and the second phase are each produced using a plurality of anodes and a plurality of cathodes of the electrode arrangement, and wherein each anode used to produce the first phase is used as a cathode to produce the second phase, and each cathode used to produce the first phase is used as an anode to produce the second phase, and wherein through each one of the individual electrodes, a first quantity of charge of the first polarity is injected to the neuromodulation site during the first phase and a second quantity of charge of the second polarity is injected to the neuromodulation site during the second phase, wherein the first quantity equals the second quantity.

In Example 14, the subject matter of Example 13 optionally includes the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

In Example 15, the subject matter of any one or more of Examples 13-14 optionally includes wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

Example 16 is an apparatus for a neuromodulation system, comprising: neuromodulation generator circuitry configured to use electrodes of an electrode arrangement to produce multi-phasic fields at a neuromodulation site; and controller circuitry configured to coordinate production of the multi-phasic fields, wherein the multi-phasic fields include: a first phase to be directed at a target region of the neuromodulation site, such that a first-polarity electrical charge is injected to the target region; and a second phase to be directed at portions of the neuromodulation site other than the target region, such that a second-polarity electrical charge opposite the first-polarity electrical charge is injected to those portions of the neuromodulation site to essentially neutralize the first-polarity charge injected at the neuromodulation site while maintaining at least a portion of the first-polarity charge at the target region.

In Example 17, the subject matter of Example 16 optionally includes the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

In Example 18, the subject matter of Example 17 optionally includes the bioelectric neuromodulation effect including one of: hyperpolarization, or partial depolarization, of neural tissue of the target region to produce a pain-suppressive therapeutic effect.

In Example 19, the subject matter of any one or more of Examples 17-18 optionally includes the bioelectric neuromodulation effect including a sub-perception polarization of neural tissue of the target region to produce a pain-suppressive therapeutic effect.

In Example 20, the subject matter of any one or more of Examples 16-19 optionally includes the first-polarity electrical charge injected to the target region in the first phase producing a first bioelectric neuromodulation effect in the target region, and wherein the second-polarity electrical charge injected to the neuromodulation site causes a second bioelectric neuromodulation effect outside of the target region.

In Example 21, the subject matter of any one or more of Examples 16-20 optionally includes each of the first phase and the second phase having a corresponding field shape that is produced by fractional energization of a plurality of individual electrodes.

In Example 22, the subject matter of any one or more of Examples 16-21 optionally includes the first phase being directed primarily the target region including pre-synaptic terminals of the dorsal horn or of the afferent nerve fibers, and the second phase being directed primarily at dorsal structures.

In Example 23, the subject matter of any one or more of Examples 16-22 optionally includes the first phase and the second phase each being produced using a plurality of anodes and a plurality of cathodes of the electrode configuration, and wherein each anode used to produce the first phase is used as a cathode to produce the second phase, and each cathode used to produce the first phase is used as an anode to produce the second phase.

In Example 24, the subject matter of Example 23 optionally includes a first quantity of charge of the first polarity injected to the neuromodulation site during the first phase and a second quantity of charge of the second polarity injected to the neuromodulation site during the second phase, wherein the first quantity equals the second quantity.

In Example 25, the subject matter of any one or more of Examples 16-24 optionally includes the first phase including a sub-threshold pulse having a first duration, and the second phase including a plurality of pulses, each of which has a duration shorter than the first duration.

Example 26 is an apparatus for a neuromodulation system, comprising: neuromodulation generator circuitry configured to use electrodes of an electrode arrangement to produce multi-phasic fields at a neuromodulation site; and controller circuitry configured to coordinate production of the multi-phasic fields, wherein the multi-phasic fields include: a first phase to be directed at a target region of the neuromodulation site, such that a first-polarity electrical charge is injected to the target region; and a second phase to be directed at portions of the neuromodulation site other than the target region, such that a second-polarity electrical charge opposite the first-polarity electrical charge is injected to those portions of the neuromodulation site; wherein the first phase and the second phase are each produced using a plurality of anodes and a plurality of cathodes of the electrode configuration, and wherein each anode used to produce the first phase is used as a cathode to produce the second phase, and each cathode used to produce the first phase is used as an anode to produce the second phase, and wherein through each one of the individual electrodes, a first quantity of charge of the first polarity is injected to the neuromodulation site during the first phase and a second quantity of charge of the second polarity is injected to the neuromodulation site during the second phase, wherein the first quantity equals the second quantity.

In Example 27, the subject matter of Example 26 optionally includes the first-polarity electrical charge injected to the target region in the first phase producing a bioelectric neuromodulation effect in the target region, and wherein the second-polarity electrical charge injected to the neuromodulation site avoids counteracting the bioelectric neuromodulation effect.

In Example 28, the subject matter of any one or more of Examples 26-27 optionally includes the first-polarity electrical charge injected to the target region in the first phase producing a first bioelectric neuromodulation effect in the target region, and wherein the second-polarity electrical charge injected to the neuromodulation site causes a second bioelectric neuromodulation effect outside of the target region.

In Example 29, the subject matter of any one or more of Examples 26-28 optionally includes each of the first phase and the second phase having a corresponding field shape that is produced by fractional energization of a plurality of individual electrodes.

In Example 30, the subject matter of any one or more of Examples 26-29 optionally includes the first phase being directed primarily the target region including pre-synaptic terminals of the dorsal horn or of the afferent nerve fibers, and the second phase being directed primarily at dorsal structures.

Example 31 is a method for operating a neuromodulation system to produce multi-phasic fields at a neuromodulation site using a set of electrodes of an electrode arrangement, the method comprising: applying a first phase of the multi-phasic fields to be directed at a target region of the neuromodulation site, such that a first-polarity electrical charge is injected to the target region; and applying a second phase of the multi-phasic fields to be directed at portions of the neuromodulation site other than the target region, such that a second-polarity electrical charge opposite the first-polarity electrical charge is injected to those portions of the neuromodulation site to essentially neutralize the first-polarity charge injected at the neuromodulation site while maintaining at least a portion of the first-polarity charge at the target region.

In Example 32, the subject matter of Example 31 optionally includes the first-polarity electrical charge being injected to the target region in the first phase to produce a bioelectric neuromodulation effect in the target region, and wherein the second-polarity electrical charge injected to the neuromodulation site avoids counteracting the bioelectric neuromodulation effect.

In Example 33, the subject matter of any one or more of Examples 31-32 optionally includes the first-polarity electrical charge injected to the target region in the first phase producing a first bioelectric neuromodulation effect in the target region, and wherein the second-polarity electrical charge injected to the neuromodulation site causes a second bioelectric neuromodulation effect outside of the target region.

In Example 34, the subject matter of any one or more of Examples 31-33 optionally includes the first phase and the second phase each being produced using a plurality of anodes and a plurality of cathodes of the electrode arrangement, and wherein each anode used to produce the first phase is used as a cathode to produce the second phase, and each cathode used to produce the first phase is used as an anode to produce the second phase.

In Example 35, the subject matter of Example 34 optionally includes a first quantity of charge of the first polarity is injected to the neuromodulation site through each one of the individual electrodes during the first phase and a second quantity of charge of the second polarity is injected to the neuromodulation site during the second phase, wherein the first quantity equals the second quantity.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 7 illustrates, by way of example, some features of the neuromodulation leads and a waveform generator.

FIG. 8 is a schematic view of a single electrical modulation lead implanted over approximately the longitudinal midline of the patient's spinal cord.

FIG. 9 illustrates an embodiment where an electrical modulation lead has been implanted more laterally with respect to the spinal cord, thereby placing it proximate the dorsal horn of the spinal cord, and the other electrical modulation lead has been implanted more medially with respect to the spinal cord, thereby placing it proximate the dorsal column of the spinal cord.

FIGS. 18A-18B illustrate, by way of example, mapping a target electrical field to an electrode array.

FIGS. 19A-19C, illustrate, by way of example, selection of a plurality of constituent current sources at the locations of the electrodes.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
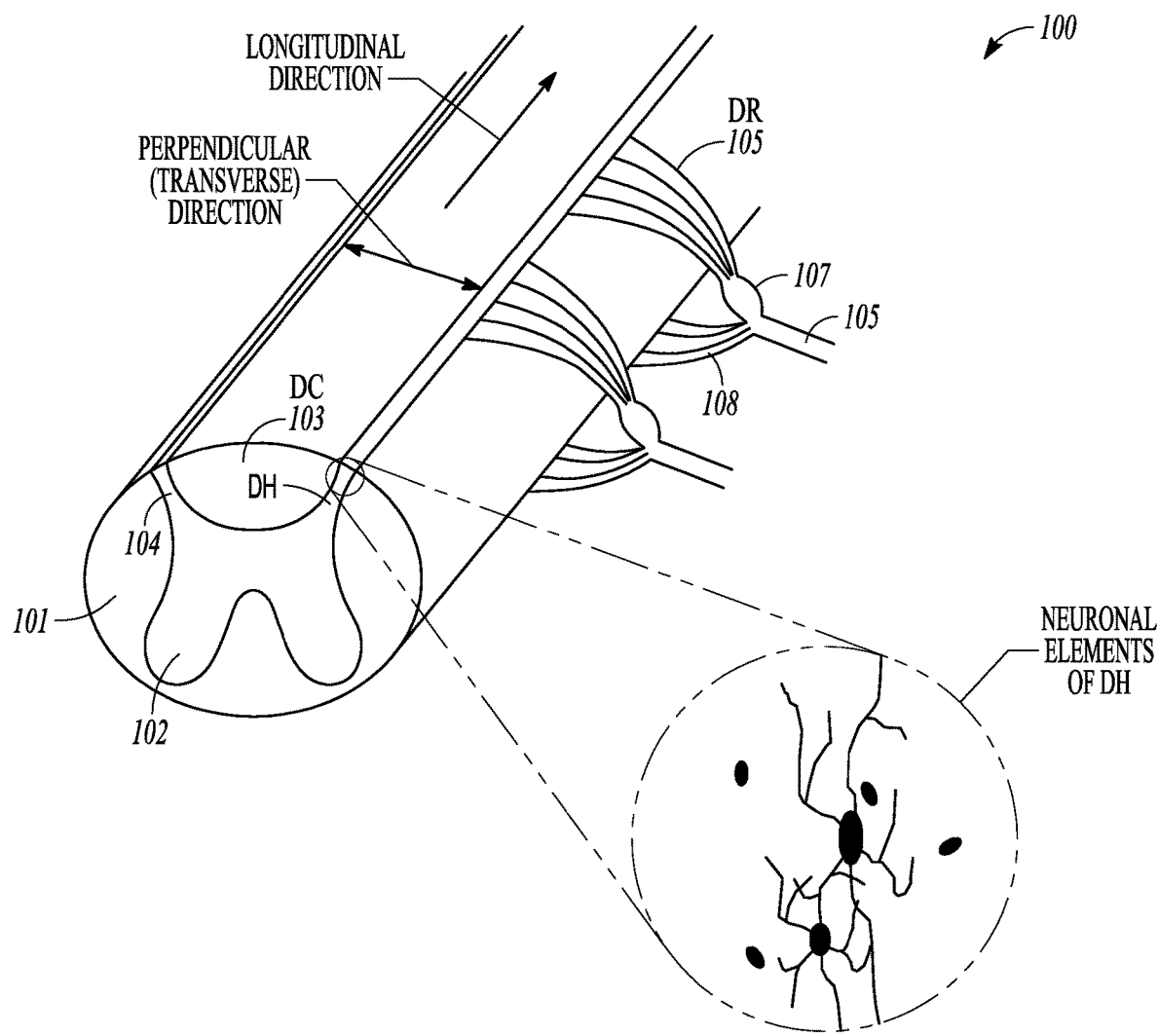
FIG. 1 illustrates, by way of example, a portion of a spinal cord.

Various embodiments described herein involve spinal cord modulation. It will be understood that principles of the embodiments may also be applied in other types of neuromodulation therapies including, but not limited to, deep brain stimulation, peripheral nerve modulation, and the like. However, for the sake of brevity, the examples described below will be in the context of spinal cord stimulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been conventionally targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases. Some embodiments deliver sub-perception therapy that is therapeutically effective to treat pain, for example, but the patient does not sense the delivery of the modulation field (e.g. paresthesia). Sub-perception therapy may include higher frequency modulation (e.g. about 1000 Hz or above) of the spinal cord that effectively blocks the transmission of pain signals in the afferent fibers in the DC. Some embodiments may implement this higher frequency modulation may include 1200 Hz or above, and some embodiments may implement this higher frequency modulation may include 1500 Hz or above. Some embodiments herein selectively modulate DH tissue, such as the presynaptic terminals of pain inhibitory neurons in the spinal cord, over DC tissue. Some embodiments selectively stimulate DR tissue and/or dorsal root ganglion over DC tissue to provide sub-perception therapy. As will be described in further detail below, some embodiments described herein target axons from inhibitory interneurons that propagate in anterior-posterior direction aligned with an electric field. Certain myelinated presynaptic terminals of inhibitory neurons oriented in the anterior-posterior (AP) direction, i.e. in parallel with electric field, may polarize more than their unmyelinated, differently oriented counterparts. Polarization may produce both subthreshold and suprathreshold effects that result in positive clinical effects, and sub-threshold progressive effects may also explain clinical observations of wash-in and wash-out effects. The terminal appears to may be the point of the greatest polarization. The unmyelinated dendrites to not polarize as much.

Such selective modulation is not delivered at these higher frequencies. For example, the selective modulation may be delivered at frequencies less than 1,200 Hz. The selective modulation may be delivered at frequencies less than 1,000 Hz in some embodiments. In some embodiments, the selective modulation may be delivered at frequencies less than 500 Hz. In some embodiments, the selective modulation may be delivered at frequencies less than 350 Hz. In some embodiments, the selective modulation may be delivered at frequencies less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle. The selected modulation may be delivered with fixed widths. Although the target filed can be applied any pulse width that the device is capable of delivering, longer pulses widths are believed to be more effective.

Figure 2:
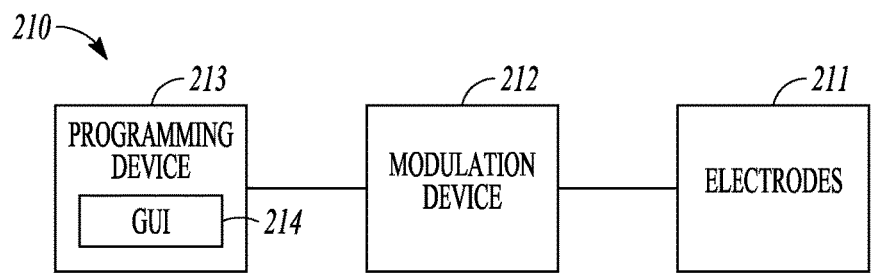
FIG. 2 illustrates, by way of example, an embodiment of a neuromodulation system.

FIG. 2 illustrates, by way of example, an embodiment of a neuromodulation system. The illustrated system 210 includes electrodes 211, a modulation device 212, and a programming system such as a programming device 213. The programming system may include multiple devices. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters. The modulation parameters may specify the electrical waveform (e.g. pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
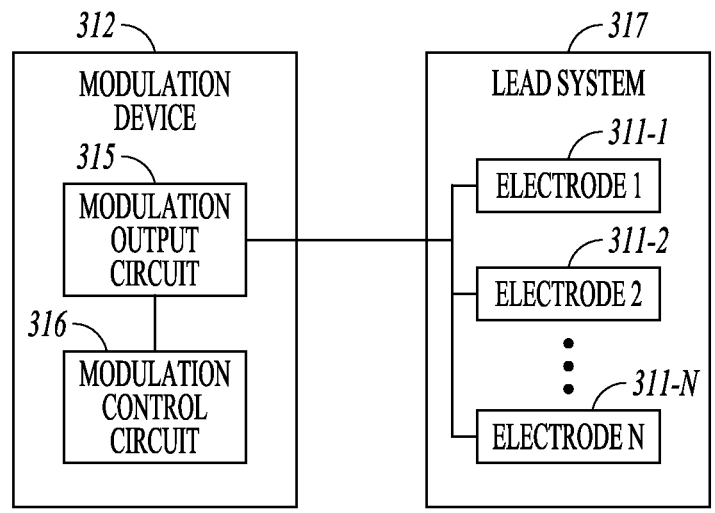
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers the neuromodulation. Neuromodulation pulses are provided herein as an example. However, the present subject matter is not limited to pulses, but may include other electrical waveforms (e.g. waveforms with different waveform shapes, and waveforms with various pulse patterns). The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient, where N≥2. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g. pulses), presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Figure 4:
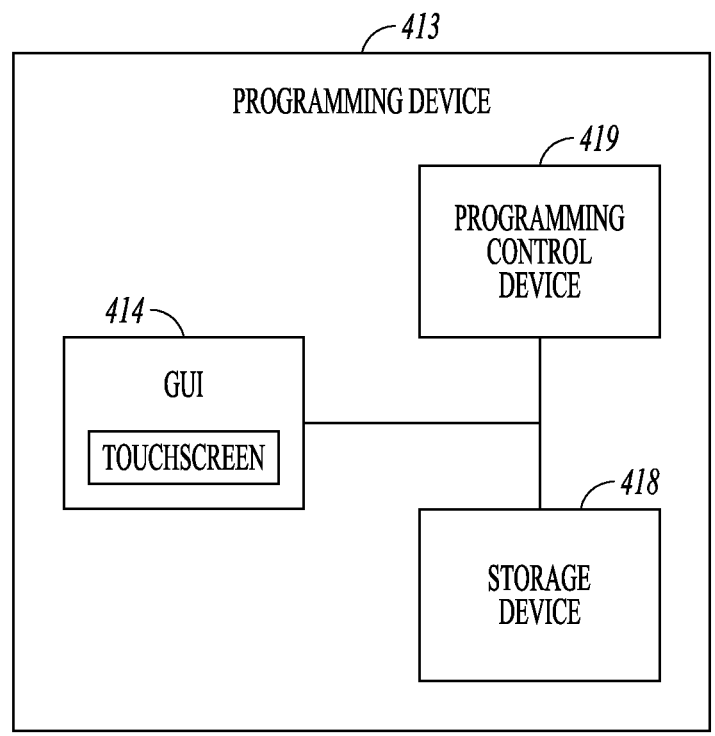
FIG. 4 illustrates, by way of example, an embodiment of a programming system such as a programming device, which may be implemented as the programming device in the neuromodulation system of FIG. 2.

FIG. 4 illustrates an embodiment of a programming system such as a programming device 413, which may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
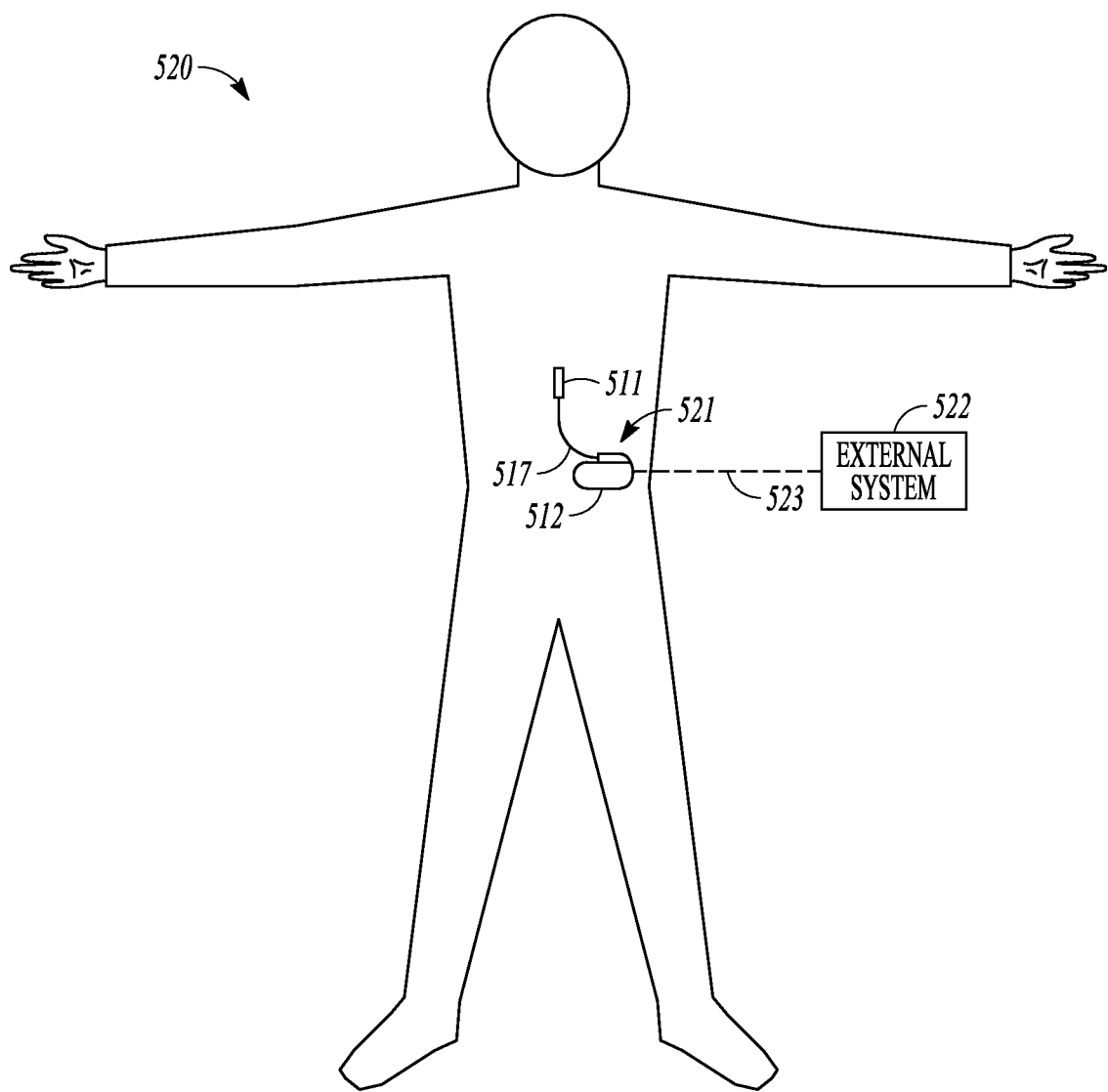
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 522 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
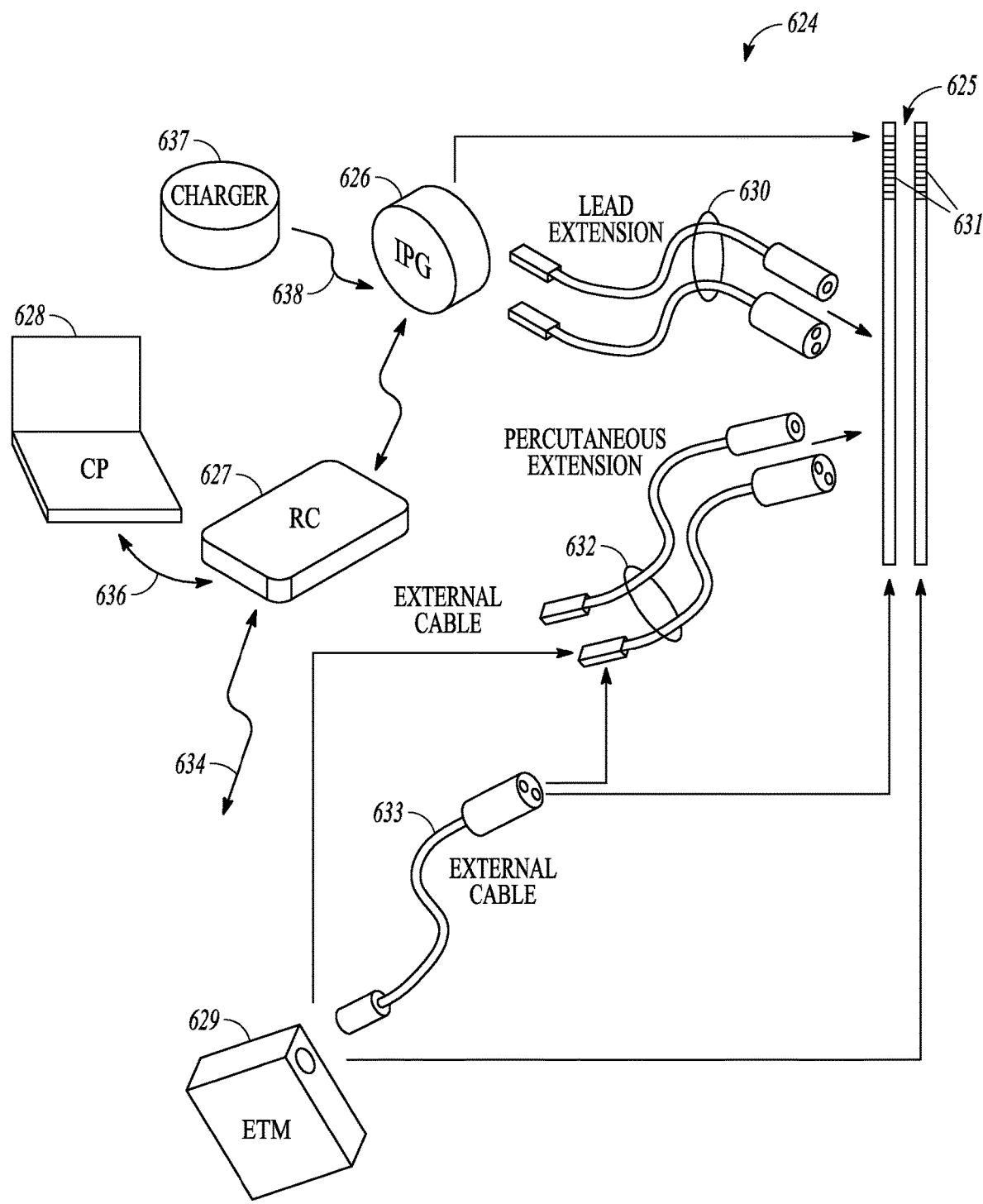
FIG. 6 illustrates, by way of example, an embodiment of a SCS system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an electrical waveform generator 626, an external remote controller RC 627, a clinician's programmer (CP) 628, and an external trial modulator (ETM) 629. IPGs are used herein as an example of the electrical waveform generator. However, it is expressly noted that the waveform generator may be configured to deliver repeating patterns of pulses, irregular patterns of pulses where pulses have differing amplitudes, pulse widths, pulse intervals, and bursts with differing number of pulses. It is also expressly noted that the waveform generator may be configured to deliver electrical waveforms other than pulses. The waveform generator 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the waveform generator case function as a case electrode) to allow for lateral steering of the current. Alternatively, a surgical paddle lead can be used in place of one or more of the percutaneous leads. In some embodiments, the waveform generator 626 may include pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar waveform generation circuitry as the waveform generator 626 to deliver electrical modulation energy to the electrodes accordance with a set of modulation parameters. The ETM 629 is a non-implantable device that is used on a trial basis after the neuromodulation leads 625 have been implanted and prior to implantation of the waveform generator 626, to test the responsiveness of the modulation that is to be provided. Functions described herein with respect to the waveform generator 626 can likewise be performed with respect to the ETM 629.

The RC 627 may be used to telemetrically control the ETM 629 via a bi-directional RF communications link 634. The RC 627 may be used to telemetrically control the waveform generator 626 via a bi-directional RF communications link 635. Such control allows the waveform generator 626 to be turned on or off and to be programmed with different modulation parameter sets. The waveform generator 626 may also be operated to modify the programmed modulation parameters to actively control the characteristics of the electrical modulation energy output by the waveform generator 626. A clinician may use the CP 628 to program modulation parameters into the waveform generator 626 and ETM 629 in the operating room and in follow-up sessions.

The CP 628 may indirectly communicate with the waveform generator 626 or ETM 629, through the RC 627, via an IR communications link 636 or other link. The CP 628 may directly communicate with the waveform generator 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the waveform generator 626 to allow the desired parameters to be determined based on patient feedback or other feedback and for subsequently programming the waveform generator 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant waveform generator, implant waveform generator and lead(s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 637 may be a portable device used to transcutaneously charge the waveform generator via a wireless link such as an inductive link 638. Once the waveform generator has been programmed, and its power source has been charged by the external charger or otherwise replenished, the waveform generator may function as programmed without the RC or CP being present.

FIG. 7 illustrates, by way of example, some features of the neuromodulation leads 725 and a waveform generator 726. The waveform generator 726 may be an implantable device or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable waveform generator may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The waveform generator may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the waveform generator. Electrical modulation energy is provided to the electrodes in accordance with a set of modulation parameters programmed into the pulse generator. By way of example but not limitation, the electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the case of the waveform generator. The system may be capable of transmitting modulation energy to the tissue in a monopolar or multipolar (e.g., bipolar, tripolar, etc.) fashion. Monopolar modulation occurs when a selected one of the lead electrodes is activated along with the case of the waveform generator, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

FIGS. 8-11 illustrate, by way of example, a difference in electrical field strength in the longitudinal and transverse directions when the current is fractionalized such that the electrical field in the longitudinal direction generated by the fractionalized current delivered to each electrode is approximately equal. The voltage at a patient's spinal cord (especially at the DC fibers) is approximately equal in the longitudinal direction, resulting in a voltage gradient of approximately zero along the DC. This may require different amounts of fractionalized current delivered to each electrode. Calibration techniques are used to determine the proper current fractionalization. With the current fractionalized to a plurality of electrodes on the electrical modulation lead, the resulting field can be calculated by superimposing the fields generated by the current delivered to each electrode. Moreover each electrical field has a longitudinal component and a transverse component.

FIG. 8 is a schematic view of a single electrical modulation lead 839 implanted over approximately the longitudinal midline of the patient's spinal cord 840. It is understood that additional leads or lead paddle(s) may be used, such as may be used to provide a wider electrode arrangement and/or to provide the electrodes closer to dorsal horn elements, and that these electrode arrays also may implement fractionalized current. FIG. 9 illustrates an embodiment where an electrical modulation lead 941 has been implanted more laterally with respect to the spinal cord, thereby placing it proximate the dorsal horn of the spinal cord, and the other electrical modulation lead 942 has been implanted more medially with respect to the spinal cord, thereby placing it proximate the dorsal column of the spinal cord 940. Placement of the lead more proximate to the DH than the DC may be desirable to preferentially stimulate DH elements over DC neural elements for a sub-perception therapy. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8. Some embodiments may include directional leads with one or more directional electrodes. A directional electrode may extend less than 360 degrees about the circumference of a lead body. For example, a row of two or more directional electrodes (e.g. "segmented electrodes") may be positioned along the circumference of the lead body. Activating select ones of the segmented electrodes may help extend and shape the field in a preferred direction.

Figure 10:
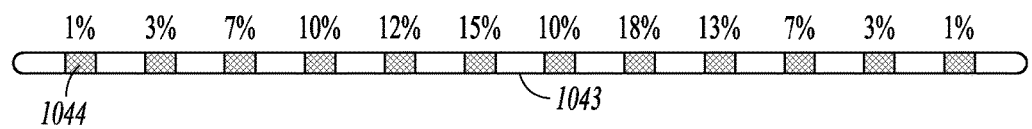
FIG. 10 is a schematic view of the electrical modulation lead showing an example of the fractionalization of the anodic current delivered to the electrodes on the electrical modulation lead.

FIG. 10 is a schematic view of the electrical modulation lead 1043 showing an example of the fractionalization of the anodic current delivered to the electrodes on the electrical modulation lead. In order to provide a simpler illustration, these figures illustrate fractionalization using monopolar modulation where a case electrode of the waveform generator is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 10, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments described herein implement a programmed algorithm to determine the appropriate fractionalization to achieve a desired modulation field property (e.g. constant electric field, or constant electric field magnitude, or constant voltage).

Figure 11:
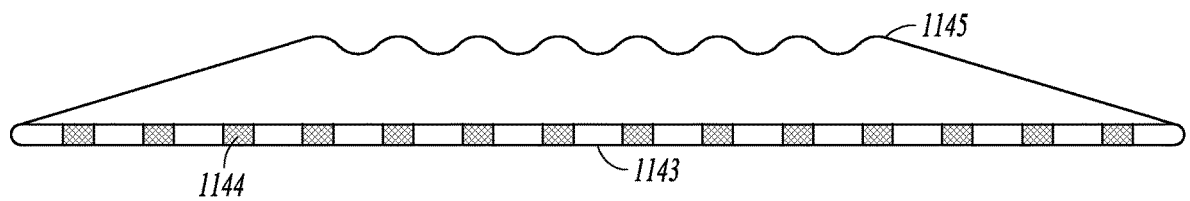
FIG. 11 illustrates, by way of example, a schematic illustration of a gradient in the longitudinal direction along the axis of the electrical modulation lead.

FIG. 11 illustrates, by way of example, a schematic illustration of a gradient in the longitudinal direction along the axis of the electrical modulation lead. The electrical field strength 1145 in the longitudinal direction is plotted over a schematic representation of the electrodes 1144 on the electrical modulation lead 1143. The illustration in FIG. 11 shows that the electrical field strength is substantially constant over the middle portion of the electrical modulation lead, but may form a wave with very small amplitude because of the gaps between the electrodes in the lead. This substantially constant electrical field forms a small longitudinal gradient, which minimizes activation of the large myelinated axons in the dorsal column. The illustration in FIG. 11 also shows the electrical field in the longitudinal direction tapering at the ends of the electrical modulation lead.

Figure 12:
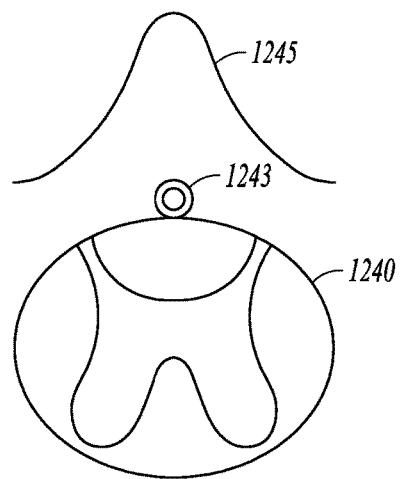
FIG. 12 illustrates, by way of example, a schematic illustration of a gradient in the transverse direction.

FIG. 12 illustrates, by way of example, a schematic illustration of a gradient in the transverse direction. The transverse electrical field strength 1245 in the transverse direction is plotted over a schematic representation of the electrical modulation lead 1243 and the spinal cord 1240 of the patient. The illustration in FIG. 12 shows that the transverse electrical field strength is greatest adjacent the electrical modulation lead and falls off lateral of the electrical modulation lead. Use of additional modulation leads to widen the electrode array may be used to provide desired fractionalization to also provide a region of a substantially constant electric field for a distance along the transverse direction. Substantially constant electric fields favor modulation of dorsal horn and/or dorsal root neuronal elements over dorsal column neuronal elements. Various embodiments use a substantially constant electric field to target inhibitory interneurons that propagate in anterior-posterior direction.

Figure 13:
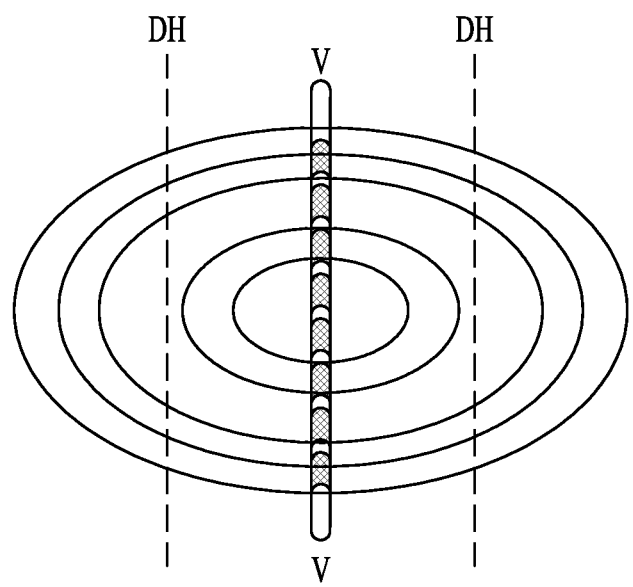
FIG. 13 illustrates, by way of example, equipotential voltage lines for a lead, along with a representation of the lead and the dorsal horns.
Figure 14:
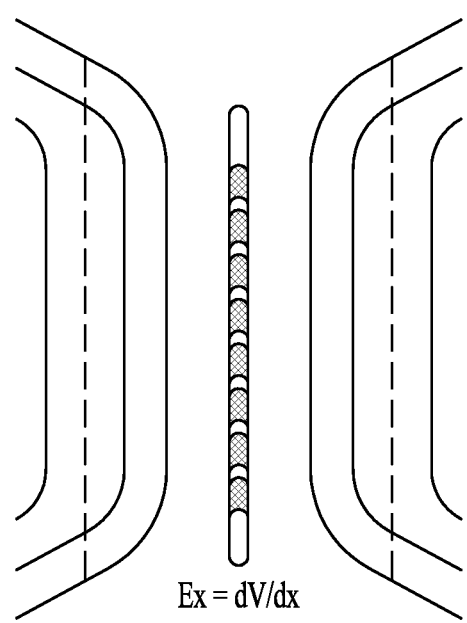
FIGS. 14-15 illustrate, by way of example, a substantial uniform electric field, along with a representation of the lead and the dorsal horns.
Figure 15:
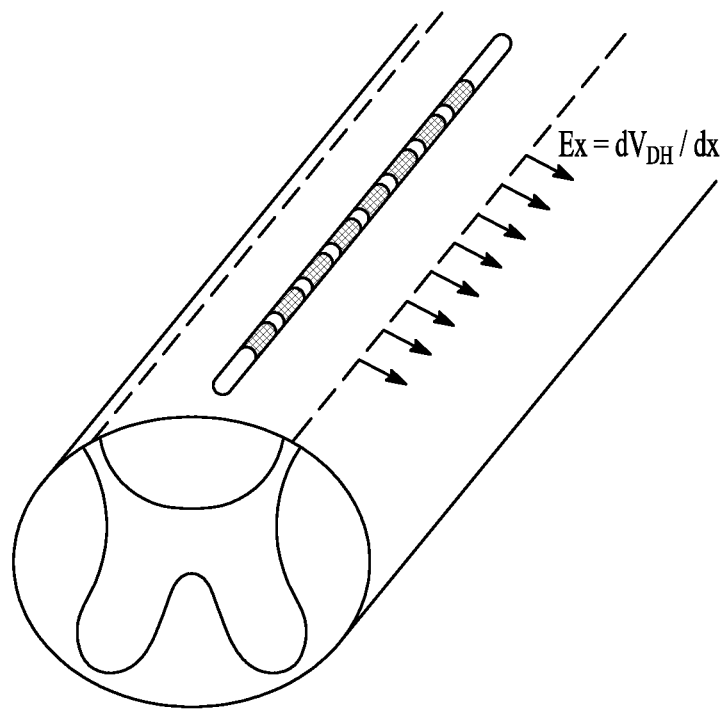

FIG. 13 illustrates, by way of example, equipotential voltage lines for a lead, along with a representation of the lead and the dorsal horns; and FIGS. 14-15 illustrate, by way of example, a substantial uniform electric field, along with a representation of the lead and the dorsal horns. The orientation of the electrical field may be selected to target the different directions/orientations of the DH elements. To generate electrical fields in different medio-lateral directions, the electrodes may have different current fractionalizations in the radial direction.

The SCS system may be configured to deliver different electrical fields to achieve a temporal summation of modulation in the DH elements. For embodiments that use a pulse generator, the electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

An embodiment modifies the fractionalized current delivered to each electrode to minimize the electrical field gradient in the longitudinal direction, so as to minimize activation of the DC elements. Minimizing activation of the DC elements can include a model-based calculation, where the model includes the information from the calibration. A discrete activating function can be calculated by the formula: $AF(n) = Ga/(\pi \times d \times 1) \times [Ve(n-1) - 2\,Ve(n) + Ve(n+1)]$, wherein Ga is the axonal intermodal conductance, d is the axonal diameter, l is the length of the node of Ranvier, $Ve(n)$ is the strength of the electric field at the node for which the activating function is determined, $Ve(n-1)$ is the strength of the electric field at the node preceding the node for which the activating function is determined, and $Ve(n+1)$ is the strength of the electric field at the node following the node for which the activating function is determined. Using this formula, the discrete activating function is calculated from the conductance normalized to the surface area of the node of Ranvier.

Modulation thresholds vary from patient to patient and from electrode to electrode within a patient. An electrode/tissue coupling calibration of the electrodes may be performed to account for these different modulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the modulation signal strength of the electrical pulse train delivered when the control element is actuated. Other sensed parameter or patient-perceived modulation values (e.g. constant paresthesia, or maximum tolerable paresthesia) may be used to provide the electrode/tissue coupling calibration of the electrodes. These sensed parameter or patient-perceived modulation values may be used to estimate the current fractionalization by minimizing the sum of the square of the discrete activating function divided by the determined value (e.g. perception threshold) at each electrode on an electrical modulation lead as is described in more detail below. Squaring the discrete activating function, or any driving force from the electrical field, eliminates the differences in depolarizing and hyperpolarizing fields. The current fractionalization that results in a minimize sum minimizes the field gradient in the longitudinal direction.

Various embodiments of the present subject matter may use "target multipoles" to provide a linear field that may maximize the electric field in a region while minimizing the activation of dorsal columns. These target multipoles may be referred to as "ideal" or "virtual" multipoles. Each target pole of a target multipole may correspond to one physical electrode, but may also correspond to a space that does not correspond to one electrode, and may be emulated using electrode fractionalization. By way of examples, U.S. Pat. Nos. 8,412,345 and 8,909,350 describe target multipoles. U.S. Pat. Nos. 8,412,345 and 8,909,350 are hereby incorporated by reference. Target multipoles are briefly described herein.

A stimulation target in the form of a target poles (e.g., a target multipole such as a target bipole or target tripole or a target multipole with more than three target poles) may be defined and the stimulation parameters, including the fractionalized current values on each of the electrodes, may be computationally determined in a manner that emulates these target poles. Current steering may be implemented by moving the target poles about the leads, such that the appropriate fractionalized current values for the electrodes are computed for each of the various positions of the target pole.

Figure 16A:
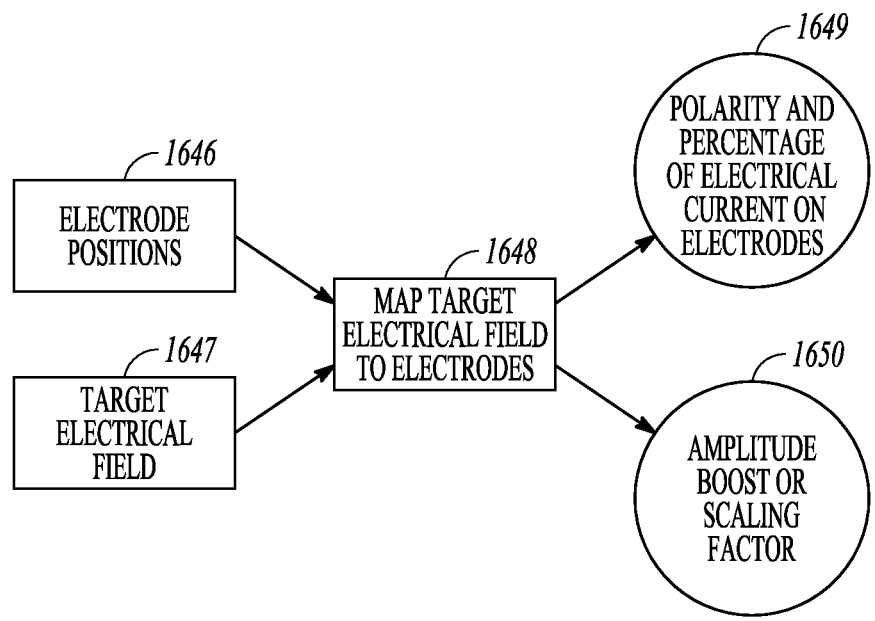
FIG. 16A illustrates, by way of example, mapping of target electrical fields to electrodes.

With reference to FIG. 16A, the CP may be configured to accept relative electrode positions 1646 and a representation of an target electrical field 1647 (instead of including these parameters in the design of navigation tables) and map the target electrical field to the electrodes 1648, thereby yielding the polarities and percentages of electrical current to be associated with the electrodes 1649, as well as a boost or scaling factor 1650 for globally adjusting the magnitude of the total current supplied to the electrodes to maintain a perceived intensity level of the electrical stimulation. Electrode locations and information about the desired electrical field may be independently inputted into the algorithm.

Figure 16B:
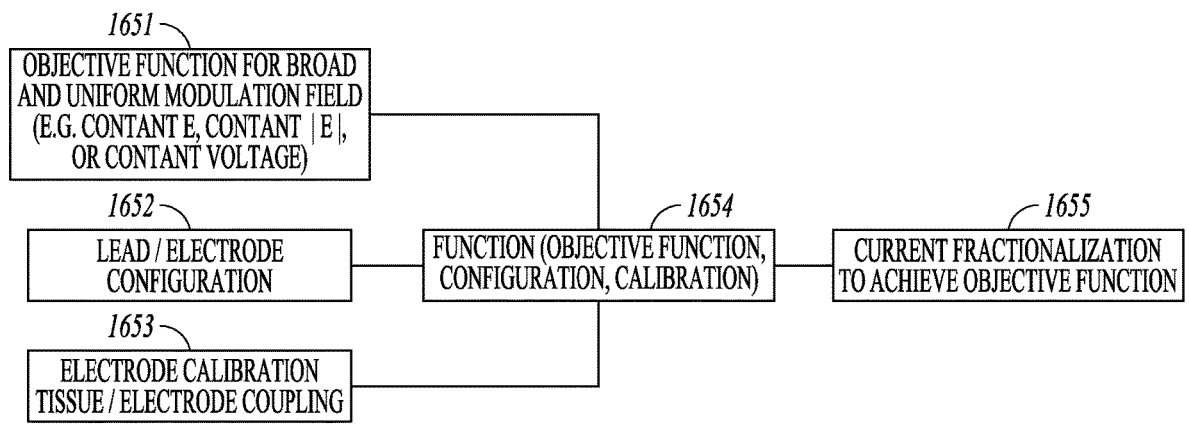
FIG. 16B illustrates, by way of example, an embodiment for determining fractionalization to achieve an objective function.

FIG. 16B illustrates, by way of example, an embodiment for determining fractionalization to achieve an objective function. An objective function refers to a function with desirable characteristics for modulating the targeted tissue. The objective function may also be referred to as an objective target function. An objective function 1651 for a broad and uniform modulation field is identified for a given volume of tissue. Examples of an objective function includes a constant E (electric field), a constant |E| (electric field magnitude), and a constant voltage. The lead and electrode configuration 1652 are also identified, as well as calibration for electrode tissue coupling 1653. A function 1654 is performed that is dependent on the objective function, the lead and electrode configuration and the calibration. The result of the function is the fractionalization of modulation energy (e.g. current) 1655 for each electrode to achieve the objective function.

Figure 17:
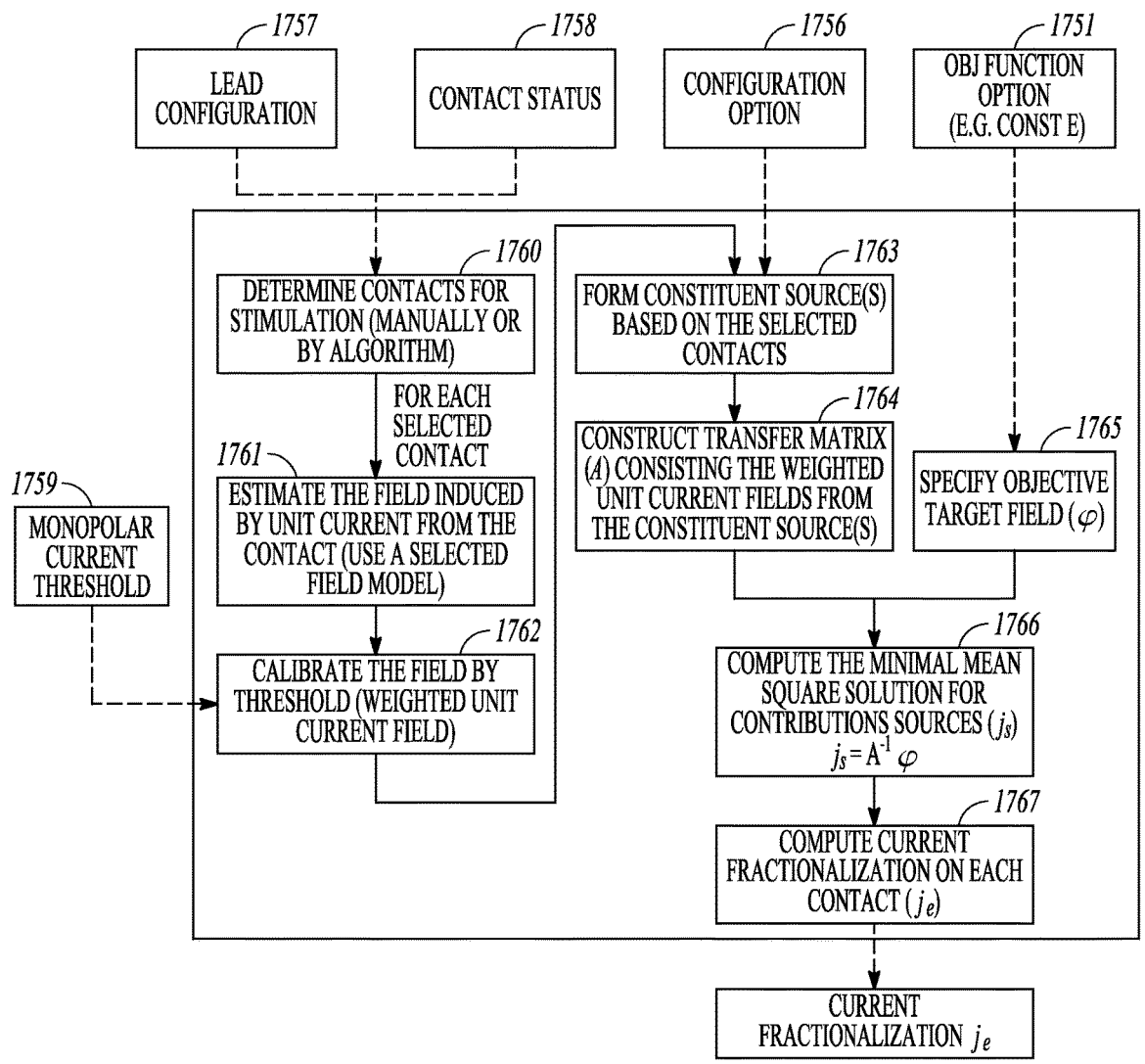
FIG. 17 illustrates, by way of example, an embodiment for determining fractionalization to achieve an objective function with more detail.

FIG. 17 illustrates, by way of example, an embodiment for determining fractionalization to achieve an objective function with more detail. An objective target function 1751 (e.g. constant E) is provided as an input to a process. Other inputs to the process include a configuration option 1756, a lead configuration 1757 and electrode contact status 1758, and a threshold 1759 such as a current threshold or more particularly a monopolar current threshold. The lead configuration 1757 and contact status 1758 identify an electrode arrangement, identifying a position of each electrode to determine the field. The overall field is a superimposed field from each electrode. The configuration option 1756 refers to monopolar (same polarity for all activated electrodes) and multipolar options (combined anode and cathodes in field). The threshold is used to compensate for electrode/tissue coupling differences.

The contacts for stimulation may be determined automatically or manually 1760 from the lead configuration and contact status. A selected field model may be used to estimate the field induced by unit current from the contact 1761. The field is calibrated using the threshold 1762. For example, the unit current field may be weighted. Constituent forces are formed based on the selected contacts 1763, and a transfer matrix 1764 is constructed to use to compute the minimal mean square solution 1766 using contributions from the constituent sources and using a specified target field 1765. The solution can be used to compute the current fractionalization on each contact 1767.

With reference to FIGS. 18A-18B, the CP may map a target electrical field to the electrode array by estimating the field potential values (or some other linear electrical parameter, such as an activating function, current density, etc.) of the target field at a plurality of spatial observation points. The CP may accomplish this by determining the desired locations of target current source poles relative to the electrode array, and modeling an electrical field generated by the target current source poles to determine desired field potential values at the spatial observation points (e.g., using analytical and/or numerical models).

Although target current source poles are one way to represent a "target electrical field", other representations of target fields may be used. The locations of the target current source poles may be determined in a manner that places the resulting electrical field over an identified region of the patient to be stimulated. The spatial observation points may be spaced in a manner that would, at the least, cover the entire tissue region to be stimulated and/or a tissue region that should not be stimulated. The locations of the target current source poles may be defined by the user, and may be displayed to the user along with the electrode locations, which as briefly discussed above, may be determined based on electrical measurements taken at the electrodes. Referring to FIGS. 19A-19C, the CP may select, or allow a user to select, a plurality of constituent current sources at the locations of the electrodes. The locations of the electrodes may be determined based on measurements taken at the electrodes in response to sub-threshold electrical signals transmitted between the electrodes. In the illustrated target bipole a first constituent current source can be defined at the locations of electrodes E1 and E2 as −100% and +100%, respectively (FIG. 19A); a second constituent current source can be defined at the locations of electrodes E2 and E3 as −100% and +100%, respectively (FIG. 19B); a third constituent current source can be defined at the locations of electrodes E3 and E4 as −100% and +100%, respectively (FIG. 19C); and so on. The location of each of the electrodes is included within at least one of the constituent sources. Thus, the minimum number of constituent sources may be equal to the number of contacts less one, or may equal the number of contacts (e.g., if a monopole is used as the constituent source).

Once the constituent sources are selected, the CP may determine the relative strengths of the constituent current sources that, when combined, result in estimated electrical field potential values at the spatial observation points that best matches the desired field potential values at the spatial observation points. In particular, the CP may model the constituent current sources (e.g., using analytical and/or numerical models) and estimate the field potential values per unit current (V/mA) generated by each of the constituent current sources at the spatial observation points, and may generate an m×n transfer matrix, for example, from the estimated field potential values per unit current, with m equaling the number of spatial observation points and n equaling the number of constituent sources. The relative strengths of the constituent current sources may be determined using an optimization function that includes the transfer matrix A and the desired field potential values.

The optimization function may be a least-squares (overdetermined) function expressed as: $|\varphi - A\hat{j}|^2$, where $\varphi$ is an m-element vector of the desired field potential values, A is the transfer matrix, and $\hat{j}$ is an n-element vector of the strengths of the constituent current sources. The constituent current source strengths $\hat{j}$ may be solved such that the optimization function $|\varphi - A\hat{j}|^2$ is minimized. The square difference is minimized if $\varphi = A\hat{j}$. One approach for solving this problem may be to invert the transfer matrix A and pre-multiply, such that $A^{-1} = \varphi A^{-1} A\hat{j}$, which yields the solution $\hat{j} = A^{-1}\varphi$. Once the strengths of the constituent current sources are determined, the CP converts these strengths to current distributions on the electrodes in the form of a polarity and percentage.

A related aspect of this disclosure relates to administering neuromodulation therapy to a localized target region to provide a beneficial bioelectric effect, such as hyper-polarization, or partial de-polarization of neural tissue, by sustaining electrical charging of a target region, while at the same time, maintaining a net-zero overall charge injection into the patient. In various embodiments, which are detailed below, multiphasic application of neuromodulation is applied, such as a biphasic application.

Notably, in various examples of the technique, the neuromodulation field of the first phase, which is referred to herein as the effectual field, has a different field configuration than that of the second phase, referred to herein as the charge-recovery field. In one type of embodiment, the target region to be stimulated is one that includes the pre-synaptic terminals of the dorsal horn. According to this type of embodiment, the target region is modulated by injecting charge using the first phase of a biphasic neuromodulation field. In a related embodiment, the target region may include presynaptic terminals of primary afferents.

The second phase of the neuromodulation field produces a charge-recovery field (or time-sequence of fields) having a different shape, and different waveform characteristics from the principal neuromodulation field, such that the charge injected to the target region by the first phase is not canceled out (in the target region) even though the charge-recovery field injects an equal amount of opposite-polarity charge such that the overall charge injected by the biphasic neuromodulation field sums to essentially zero.

In an example, the charge-recovery field may be directed primarily at the dorsal column. Direction of a field in the present context refers to the region where the field is primarily positioned, or concentrated. In some cases the effectual field and the charge-recovery field may spatially overlap to some extent, and the charge-recovery field may reduce the charge injected into the target region by the effectual field. However, according to various embodiments, in spite of the spatial overlap, some portion of the charge injected by the effectual field remains at the target region. In another example, the charge-recovery field may be directed at the dorsal root region if the field is not amenable to dorsal root stimulation.

In a related embodiment, the effectual field and the charge-recovery field have substantially different waveforms, such that the bioelectric neuromodulation effect induced by the effectual field is not significantly counteracted by the charge-recovery field. In some embodiments, the charge-recovery field of the second phase may have waveform and field characteristics to provide a second neuromodulation effect that may be distinct from the neuromodulation effect of the effectual field of the first phase. For instance, the charge-recovery field may be used to administer paresthesia or other supraperception therapy.

Figure 20:
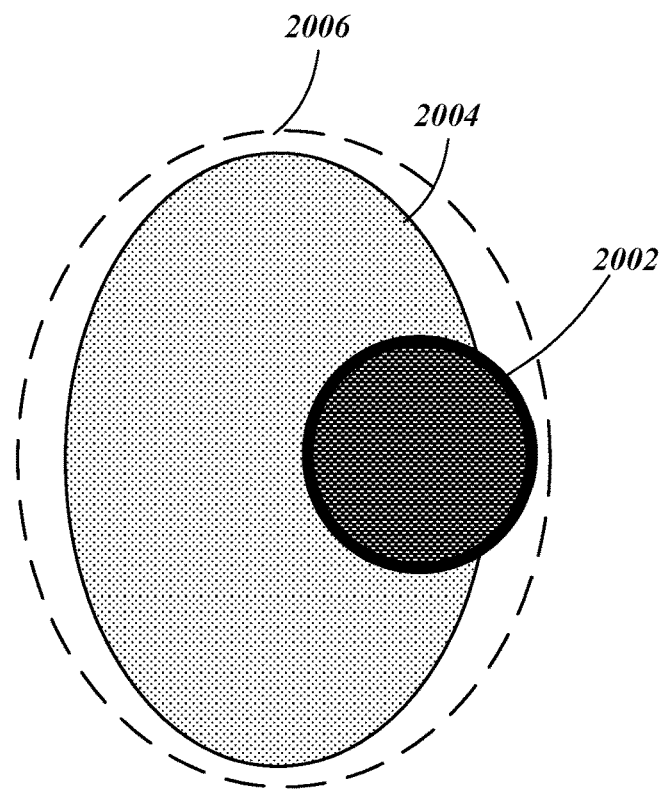
FIG. 20 is a schematic diagram illustrating an example spatial relationship between the fields of a first phase and a second phase of a biphasic application of electrotherapy signaling according to some aspects of the embodiments.

FIG. 20 is a schematic diagram illustrating an example spatial relationship between the fields of a first phase and a second phase of a biphasic application of electrotherapy signaling according to some aspects of the embodiments. As depicted, the effectual field 2002 having a first polarity is applied to the target region (e.g., the dorsal horn) in the first phase. In a subsequent second phase, charge-recovery field 2004 is applied. Charge-recovery field 2004 has the opposite polarity of effectual field 2002. In the illustrated schematic example, charge-recovery field 2004 has a different shape than effectual field 2002. Effectual field 2002 and charge-recovery field 2004, together, define a neuromodulation site 2006. Since the charge magnitudes of effectual field 2002 and charge-recovery field 2004 are practically equal, there is no net charge injected into neuromodulation site 2006 at the conclusion of the biphasic neuromodulation field application when neuromodulation site 2006 is considered as a whole. Notably, the target region to which effectual field 2002 is directed will maintain a residual charge, which provides a bioelectric neuromodulation effect such as hyperpolarization or partial depolarization for pain suppression. It will be appreciated that, with a net zero overall charge transfer, having a residual charge in the target region implies the presence of an opposite residual charge elsewhere in the neuromodulation site. According to some embodiments, the opposite-polarity residual charge outside of the target region is less concentrated than the residual charge of the target region, such that the residual charge outside the target region has no or negligible neuromodulation effect.

Figure 21:
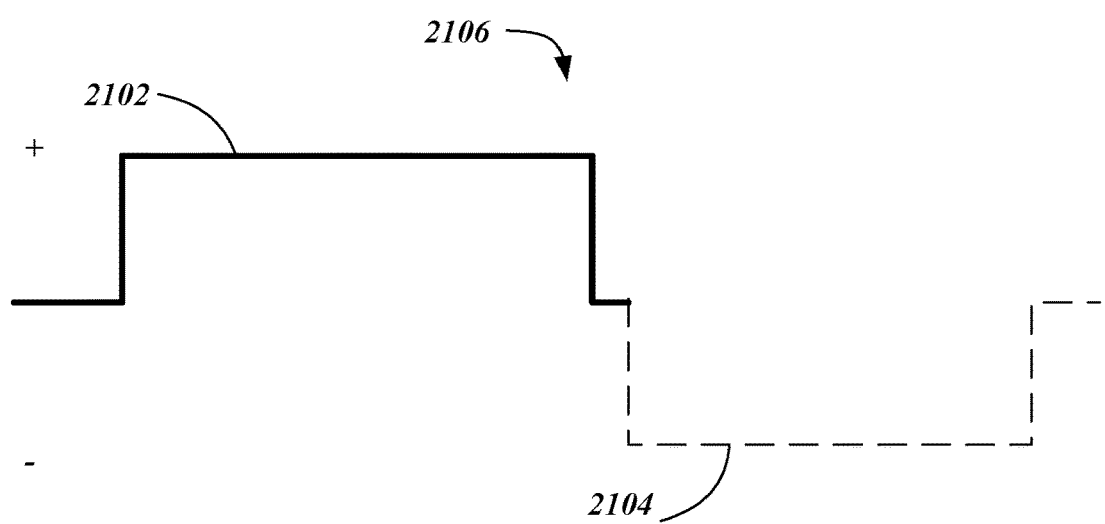
FIG. 21 is a diagram illustrating an example temporal relationship between the first phase and second phase of an overall neuromodulation field according to various embodiments.

FIG. 21 is a diagram illustrating an example temporal relationship between the first phase and the second phase of the overall neuromodulation field 2106 according to various embodiments. As depicted, the effectual field 2102 of the first phase is applied initially, followed by the charge-recovery field 2104 of the second phase. As depicted, effectual field 2102 injects charge of a first polarity (in the present example, +), whereas the charge-recovery field 2104 injects charge of the opposite polarity (in the present example, −). The charge injection may be monitored and controlled as with current and time measurement and control, since charge is defined as ampere-seconds.

In one type of embodiment, as will be described in greater detail below, effectual field 2102 is composed of one or more pulses, whereas charge-recovery field 2104 is composed of a plurality of pulses, with each pulse of the charge-recovery field 2104 being shorter in duration than each individual (one or more) pulses of the effectual field 2102. In a particular example, the effectual field 2102 consists of a single pulse having a duration of between 10 and 1000 microseconds, and charge-recovery field 2104 consists of a group of pulses, each of which is less than 10 microseconds in duration.

As discussed above, the overall charge transfer of neuromodulation field 2106, taking into account both phases, may be zero or some negligible amount. In a related embodiment (now shown) the ordering of the effectual and charge-recovery fields may be reversed, such that the charge-recovery field 2104 occurs first, followed by the effectual field 2102.

Figure 22:
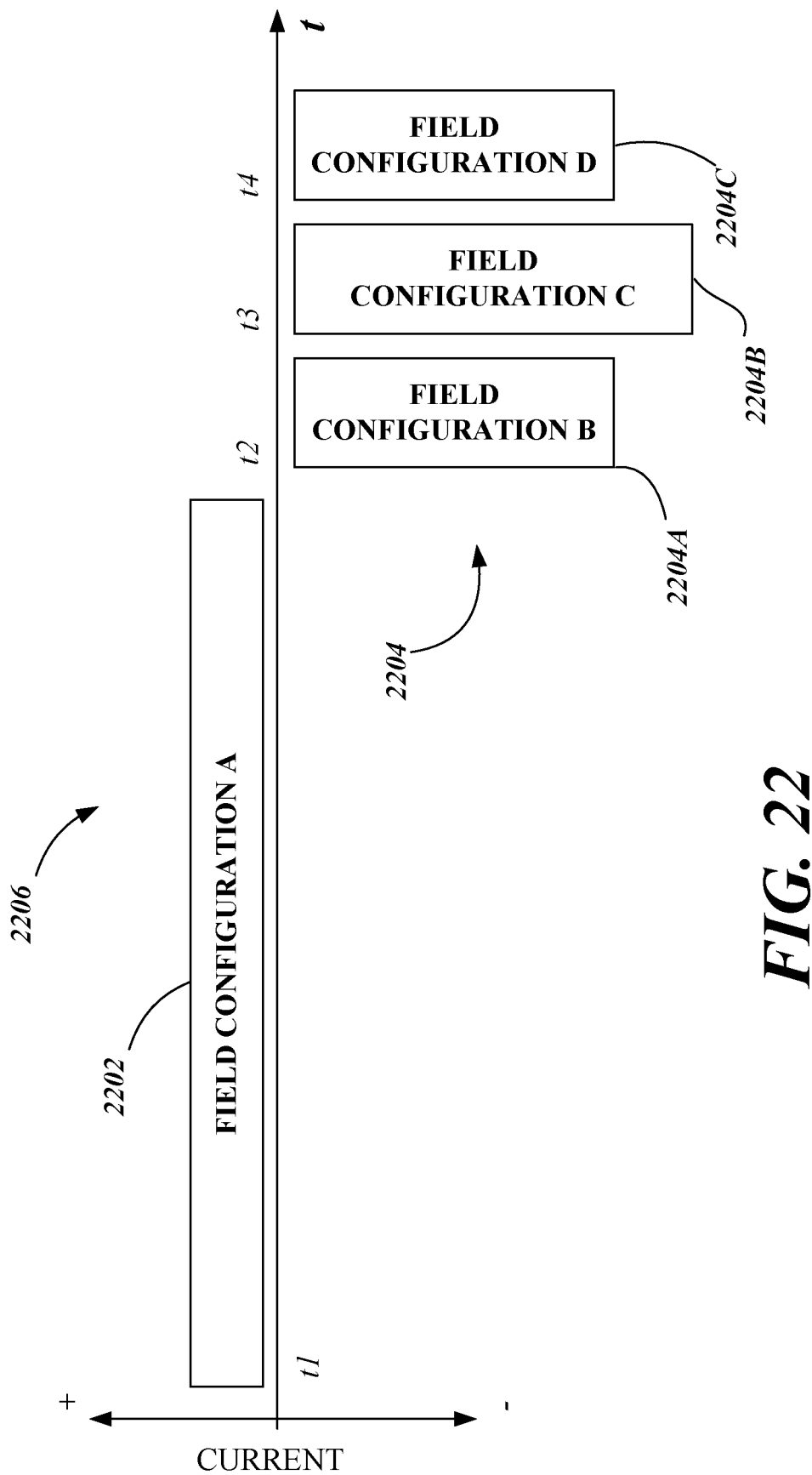
FIG. 22 is a diagram illustrating the use of multiple sequential field configurations for a charge-recovery field according to some embodiments.

FIG. 22 is a diagram illustrating the use of multiple sequential field configurations for the charge-recovery field according to some embodiments. In this diagram, time t is shown along the horizontal axis, and the applicable electrode currents from which the respective effectual and charge-recovery fields are generated are shown along the vertical axis. Biphasic neuromodulation field 2206 is composed of effectual field 2202, followed by a charge-recovery field 2204 that is composed of three segments, 2204A-2204C.

At time t1, effectual field 2202 is initiated, having a particular field configuration, indicated as field configuration A. Generally speaking, the field configuration of a given field includes the spatial shape of the field, as well as the amplitude and waveform shape. As illustrated, effectual field 2202 has a relatively lower amplitude, and a relatively longer duration than the opposite-polarity charge-recovery field 2204 composed of segments 2204A-2204C. As an example, effectual field 2202 may have a current amplitude on the order of 100 μA. Field configuration A is adapted to produce a bioelectric neuromodulation effect, such as sub-activation hyperpolarization (or partial de-polarization) of neural tissue, such as dorsal-horn tissue, to suppress pain experienced by the patient.

At time t2, following the conclusion of effectual field 2202, the first segment 2204A of charge-recovery field 2204 is initiated. First segment 2204A has a field configuration B corresponding to a particular amplitude, duration, and field shape. At time t3, following the conclusion of first segment 2204A, second segment 2204B of charge-recovery field 2204 is initiated. Second segment 2204B has a field configuration C corresponding to a particular amplitude, duration, and field shape, that differs from field configurations A and B, although it is more similar to field configuration B. Next, at time t4, following the conclusion of second segment 2204B, third segment 2204C of charge-recovery field 2204 is initiated. Third segment 2204C has a field configuration D corresponding to a particular amplitude, duration, and field shape, that differs from field configurations A-C.

Each segment 2204A-2204C injects a corresponding portion of the total charge of the charge-recovery field 2204. The total charge injected by charge-recovery field 2204 neutralizes the total charge injected by effectual field 2202 to produce a net-zero overall charge transfer from biphasic neuromodulation field 2206 to the neuromodulation site. However, because field configurations B-D each differs from field configuration A, there remains a DC charge of neural tissue at the target region to which effectual field 2202 is directed (and which charge-recovery field 2204 seeks to avoid to some extent), following the administration of biphasic neuromodulation field 2206.

It should be noted that, in some embodiments, the field configurations B-D of charge-recovery field 2204 are particularly adapted to avoid counteracting the bioelectric neuromodulation effect produced by effectual field 2202. According to some embodiments, this may be achieved by a combination of shaping and directing the charge-recovery field away from the target region, as well as selectively applying waveform characteristics to reduce or minimize producing a counteracting bioelectric effect to the desired one. In some examples, the use of multiple short pulses with various field configurations in the charge-recovery phase takes advantage of the strength-duration properties of neural tissue, which tend to exhibit reduced sensitivity to shorter pulse durations for a given pulse amplitude. Thus, the charge-recovery field 2204, having a plurality of short-duration segments 2204A-2204C, may use higher amplitudes than the effectual field 2202 to provide sufficient charge recovery, without causing undesired sensation or disruption of the desired bioelectric neuromodulation effect of the effectual field 2202.

Figure 23:
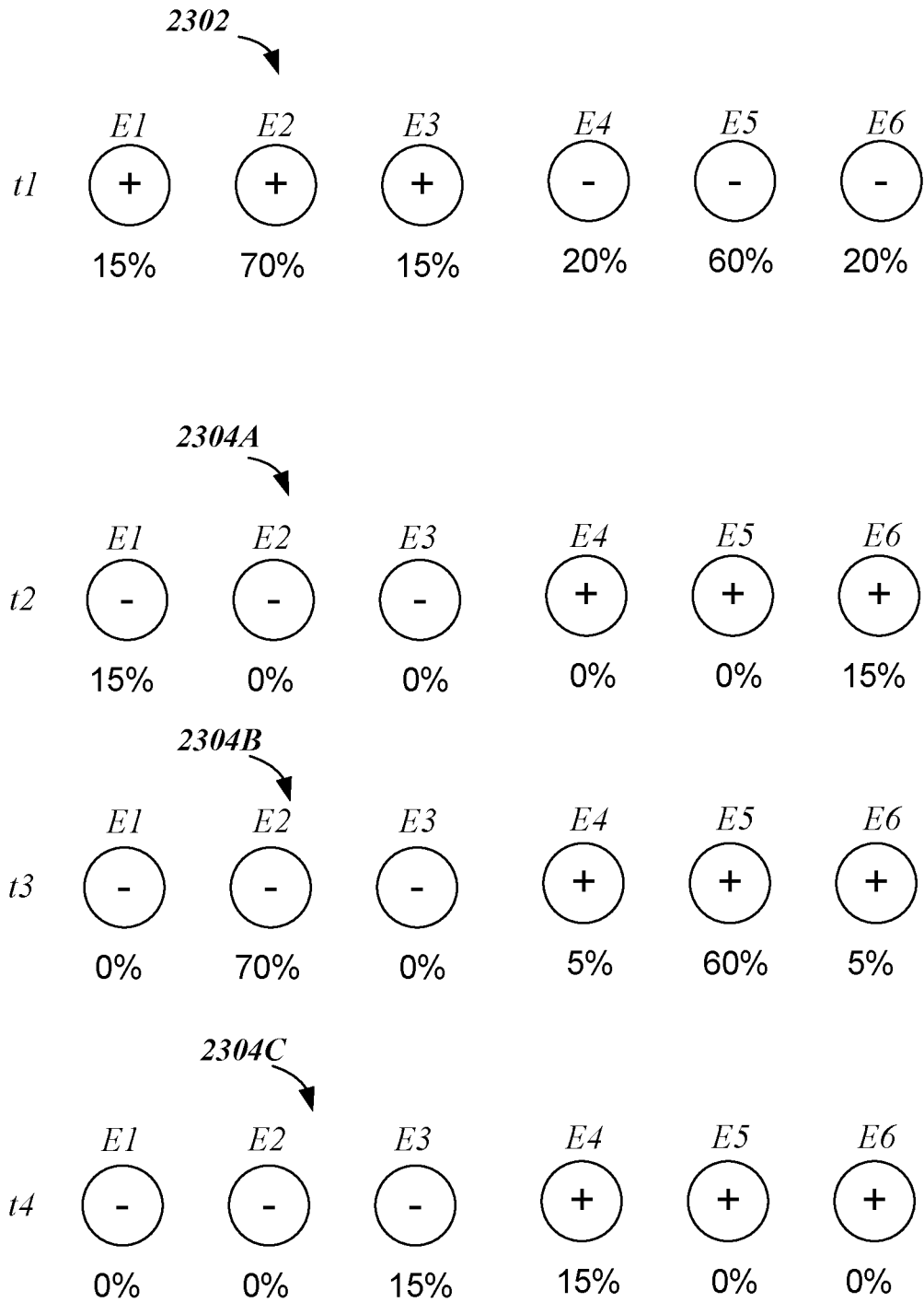
FIG. 23 is a diagram illustrating fractionalized electrode configurations for achieving various field configurations according to some embodiments.

FIG. 23 is a diagram illustrating fractionalized electrode configurations for achieving various field configurations according to some embodiments. As depicted by way of example and not limitation, electrodes E1-E6 are fractionally energized to selectively produce the various field configurations. Fractionalized electrode configuration 2302, which may be used to produce effectual field 2202 (FIG. 22) beginning at time t1, uses electrodes E1-E3 as anodes and electrodes E4-E6 as cathodes. The fractionalized percentages are indicated below each electrode's representative symbol. Notably, the fractionalized anodic currents add up to 100%, and the fractionalized cathodic currents add up to 100%. The fractionalized current distribution of {15%, 70%, 15%} for the anode and {−20%, −60%, −20%} for the cathode may be referred to as a spread-bipole configuration. It will be understood that a variety of other distributions are contemplated that may be suited to particular therapeutic objectives.

Fractionalized electrode configurations 2304A-2304C in this example correspond respectively to charge-recovery field segments 2204A-2204C. As shown in FIG. 23, each of electrodes E1-E6 has its polarity reversed for the second phase such that electrodes E1-E3 are cathodes while electrodes E4-E6 are anodes. Fractionalized electrode configuration 2304A to produce the first segment 2204A of the charge-recovery field 2204 at t2 has a current distribution of {−15%, 0%, 0%} for the cathodes E1-E3 and {0%, 0%, 15%} for the anodes E4-E6. Fractionalized electrode configuration 2304B to produce the second segment 2204B of the charge-recovery field 2204 at t3 has a current distribution of {0%, −70%, 0%} for the cathodes E1-E3 and {5%, 60%, 5%} for the anodes E4-E6. Fractionalized electrode configuration 2304C to produce the first segment 2204C of the charge-recovery field 2204 at t4 has a current distribution of {0%, 0%, −15%} for the cathodes E1-E3 and {15%, 0%, 0%} for the anodes E4-E6.

Notably, in this example, the sum of the fractionalized currents for each electrode in the second phase equals opposite-polarity of the fractionalized current of the same electrode in the first phase. Accordingly, there is essentially no residual DC charge at any of the electrodes following administration of the biphasic neuromodulation field. This is an example of embodiments in which the biphasic neuromodulation field exhibits asymmetry in the field configurations between the first and the second phases, while exhibiting electrical-current symmetry for zero net charge injection by each of the electrodes.

In addition to the Examples discussed in the Summary Section above, some other non-limiting examples are provided as follows.

Example 36 is apparatus for a neuromodulation system, comprising: neuromodulation generator circuitry configured to use electrodes of an electrode arrangement to produce multi-phasic fields at a neuromodulation site; and controller circuitry configured to coordinate production of the multi-phasic fields, wherein the multi-phasic fields include: a first phase to be directed at a target region of the neuromodulation site, such that a first-polarity electrical charge is injected to the target region; and a second phase to be directed at portions of the neuromodulation site other than the target region, such that a second-polarity electrical charge opposite the first-polarity electrical charge is injected to those portions of the neuromodulation site; wherein the first phase and the second phase are each produced using a plurality of anodes and a plurality of cathodes of the electrode configuration, and wherein each anode used to produce the first phase is used as a cathode to produce the second phase, and each cathode used to produce the first phase is used as an anode to produce the second phase, and wherein through each one of the individual electrodes, a first quantity of charge of the first polarity is injected to the neuromodulation site during the first phase and a second quantity of charge of the second polarity is injected to the neuromodulation site during the second phase, wherein the first quantity equals the second quantity.

In Example 37, the subject matter of Example 36 optionally includes wherein the second phase is subsequent to the first phase.

In Example 38, the subject matter of any one or more of Examples 36-37 optionally include wherein the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

In Example 39, the subject matter of Example 38 optionally includes wherein the bioelectric neuromodulation effect includes one of: hyperpolarization, or partial depolarization, of neural tissue of the target region to produce a pain-suppressive therapeutic effect.

In Example 40, the subject matter of any one or more of Examples 38-39 optionally include wherein the bioelectric neuromodulation effect includes a sub-perception polarization of neural tissue of the target region to produce a pain-suppressive therapeutic effect.

In Example 41, the subject matter of any one or more of Examples 36-40 optionally include wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

In Example 42, the subject matter of any one or more of Examples 36-41 optionally include wherein each of the first phase and the second phase has a corresponding field shape that is produced by fractional energization of a plurality of individual electrodes.

In Example 43, the subject matter of any one or more of Examples 36-42 optionally include wherein the first phase is directed primarily at the dorsal horn, with the target region including pre-synaptic terminals of the dorsal horn, and wherein the second phase is directed primarily at the dorsal column.

In Example 44, the subject matter of any one or more of Examples 36-43 optionally include wherein the first phase and the second phase have different field shapes and different waveforms.

In Example 45, the subject matter of any one or more of Examples 36-44 optionally include wherein the first phase includes a sub-threshold pulse having a first duration, and wherein the second phase includes a plurality of pulses, each of which has a duration shorter than the first duration. For instance, the first phase may include a sub-threshold pulse of between 10 microseconds and 1000 microseconds, and the second phase may include a plurality of pulses, each of which is shorter than 10 microseconds.

Example 46 is a method for operating a neuromodulation system to produce multi-phasic fields at a neuromodulation site using a set of electrodes of an electrode arrangement, the method comprising: applying a first phase of the multi-phasic fields to be directed at a target region of the neuromodulation site, such that a first-polarity electrical charge is injected to the target region; and applying a second phase of the multi-phasic fields to be directed at portions of the neuromodulation site other than the target region, such that a second-polarity electrical charge opposite the first-polarity electrical charge is injected to the neuromodulation site to essentially neutralize the first-polarity charge injected at the neuromodulation site while maintaining at least a portion of the first-polarity charge at the target region.

In Example 47, the subject matter of Example 46 optionally includes wherein the second phase is subsequent to the first phase.

In Example 48, the subject matter of any one or more of Examples 46-47 optionally include wherein the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

In Example 49, the subject matter of Example 48 optionally includes wherein the bioelectric neuromodulation effect includes one of: hyperpolarization, or partial depolarization, of neural tissue of the target region to produce a pain-suppressive therapeutic effect.

In Example 50, the subject matter of any one or more of Examples 48-49 optionally include wherein the bioelectric neuromodulation effect includes a sub-perception polarization of neural tissue of the target region to produce a pain-suppressive therapeutic effect.

In Example 51, the subject matter of any one or more of Examples 46-50 optionally include wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

In Example 52, the subject matter of any one or more of Examples 46-51 optionally include wherein each of the first phase and the second phase has a corresponding field shape that is produced by fractional energization of a plurality of individual electrodes.

In Example 53, the subject matter of any one or more of Examples 46-52 optionally include wherein the first phase is directed primarily at the dorsal horn, with the target region including pre-synaptic terminals of the dorsal horn, and wherein the second phase is directed primarily at the dorsal column.

In Example 54, the subject matter of any one or more of Examples 46-53 optionally include wherein the first phase and the second phase are each produced using a plurality of anodes and a plurality of cathodes of the electrode configuration, and wherein each anode used to produce the first phase is used as a cathode to produce the second phase, and each cathode used to produce the first phase is used as an anode to produce the second phase.

In Example 55, the subject matter of Example 54 optionally includes wherein through each one of the individual electrodes, a first quantity of charge of the first polarity is injected to the neuromodulation site during the first phase and a second quantity of charge of the second polarity is injected to the neuromodulation site during the second phase, wherein the first quantity equals the second quantity.

In Example 56, the subject matter of any one or more of Examples 46-55 optionally include wherein the first phase and the second phase have different field shapes and different waveforms.

In Example 57, the subject matter of any one or more of Examples 46-56 optionally include wherein the first phase includes a sub-threshold pulse having a first duration, and wherein the second phase includes a plurality of pulses, each of which has a duration shorter than the first duration. For instance, the first phase may include a sub-threshold pulse of between 10 microseconds and 1000 microseconds, and the second phase may include a plurality of pulses, each of which is shorter than 10 microseconds.

Example 58 is a method for operating a neuromodulation system to produce multi-phasic fields at a neuromodulation site using a set of electrodes of an electrode arrangement, the method comprising: applying a first phase of the multi-phasic fields to be directed at a target region of the neuromodulation site, such that a first-polarity electrical charge is injected to the target region; and applying a second phase of the multi-phasic fields to be directed at portions of the neuromodulation site other than the target region, such that a second-polarity electrical charge opposite the first-polarity electrical charge is injected to those portions of the neuromodulation site; wherein the first phase and the second phase are each produced using a plurality of anodes and a plurality of cathodes of the electrode arrangement, and wherein each anode used to produce the first phase is used as a cathode to produce the second phase, and each cathode used to produce the first phase is used as an anode to produce the second phase, and wherein through each one of the individual electrodes, a first quantity of charge of the first polarity is injected to the neuromodulation site during the first phase and a second quantity of charge of the second polarity is injected to the neuromodulation site during the second phase, wherein the first quantity equals the second quantity.

In Example 59, the subject matter of Example 58 optionally includes wherein the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

In Example 60, the subject matter of any one or more of Examples 58-59 optionally include wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

In Example 61, the subject matter of any one or more of Examples 58-60 optionally include wherein each of the first phase and the second phase has a corresponding field shape that is produced by fractional energization of a plurality of individual electrodes.

In Example 62, the subject matter of any one or more of Examples 58-61 optionally include wherein the first phase is directed primarily at the dorsal horn, with the target region including pre-synaptic terminals of the dorsal horn, and wherein the second phase is directed primarily at the dorsal column.

The above detailed description is intended to be illustrative, and not restrictive. The scope of the disclosure should, therefore, be determined with references to the appended claims, along with the full scope of equivalents to which such claims are entitled.

What is claimed is:

1. Apparatus for a neuromodulation system, comprising:
    neuromodulation generator circuitry configured to use electrodes of an electrode arrangement to produce multi-phasic fields at a neuromodulation site; and
    controller circuitry configured to coordinate production of the multi-phasic fields, wherein the multi-phasic fields include:
        a first phase to be directed at a target region of the neuromodulation site, such that a first-polarity electrical charge is injected to the target region; and
        a second phase to be directed at portions of the neuromodulation site other than the target region, such that a second-polarity electrical charge opposite the first-polarity electrical charge is injected to those portions of the neuromodulation site to essentially neutralize the first-polarity electrical charge injected at the neuromodulation site while maintaining at least a portion of the first-polarity electrical charge at the target region.

2. The apparatus of claim 1, wherein the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

3. The apparatus of claim 2, wherein the bioelectric neuromodulation effect includes one of: hyperpolarization, or partial depolarization, of neural tissue of the target region to produce a pain-suppressive therapeutic effect.

4. The apparatus of claim 2, wherein the bioelectric neuromodulation effect includes a sub-perception polarization of neural tissue of the target region to produce a pain-suppressive therapeutic effect.

5. The apparatus of claim 1, wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

6. The apparatus of claim 1, wherein each of the first phase and the second phase has a corresponding field shape that is produced by fractional energization of a plurality of individual electrodes.

7. The apparatus of claim 1, wherein the first phase is directed primarily the target region including pre-synaptic terminals of the dorsal horn or of the afferent nerve fibers, and wherein the second phase is directed primarily at dorsal structures.

8. The apparatus of claim 1, wherein the first phase and the second phase are each produced using a plurality of anodes and a plurality of cathodes of the electrode configuration, and wherein each anode used to produce the first phase is used as a cathode to produce the second phase, and each cathode used to produce the first phase is used as an anode to produce the second phase.

9. The apparatus of claim 8, wherein, through each individual electrode, a first quantity of charge of the first polarity is injected to the neuromodulation site during the first phase and a second quantity of charge of the second polarity is injected to the neuromodulation site during the second phase, wherein the first quantity equals the second quantity.

10. The apparatus of claim 1, wherein the first phase includes a sub-threshold pulse of between 10 microseconds and 1000 microseconds, and wherein the second phase includes a plurality of pulses, each of which is shorter than 10 microseconds.

11. Apparatus for a neuromodulation system, comprising:
    neuromodulation generator circuitry configured to use electrodes of an electrode arrangement to produce multi-phasic fields at a neuromodulation site; and
    controller circuitry configured to coordinate production of the multi-phasic fields, wherein the multi-phasic fields include:
        a first phase to be directed at a target region of the neuromodulation site, such that a first-polarity electrical charge is injected to the target region; and
        a second phase to be directed at portions of the neuromodulation site other than the target region, such that a second-polarity electrical charge opposite the first-polarity electrical charge is injected to those portions of the neuromodulation site;
    wherein the first phase and the second phase are each produced using a plurality of anodes and a plurality of cathodes of the electrode configuration, and wherein each anode used to produce the first phase is used as a cathode to produce the second phase, and each cathode used to produce the first phase is used as an anode to produce the second phase, and
    wherein, through each individual electrode, a first quantity of charge of the first polarity is injected to the neuromodulation site during the first phase and a second quantity of charge of the second polarity is injected to the neuromodulation site during the second phase, wherein the first quantity equals the second quantity.

12. The apparatus of claim 11, wherein the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

13. The apparatus of claim 11, wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

14. The apparatus of claim 11, wherein each of the first phase and the second phase has a corresponding field shape that is produced by fractional energization of a plurality of individual electrodes.

15. The apparatus of claim 11, wherein the first phase is directed primarily the target region including pre-synaptic terminals of the dorsal horn or of the afferent nerve fibers, and wherein the second phase is directed primarily at dorsal structures.

16. A method for operating a neuromodulation system to produce multi-phasic fields at a neuromodulation site using a set of electrodes of an electrode arrangement, the method comprising:
    applying a first phase of the multi-phasic fields to be directed at a target region of the neuromodulation site, such that a first-polarity electrical charge is injected to the target region; and
    applying a second phase of the multi-phasic fields to be directed at portions of the neuromodulation site other than the target region, such that a second-polarity electrical charge opposite the first-polarity electrical charge is injected to those portions of the neuromodulation site to essentially neutralize the first-polarity electrical charge injected at the neuromodulation site while maintaining at least a portion of the first-polarity electrical charge at the target region.

17. The method of claim 16, wherein the first-polarity electrical charge injected to the target region in the first phase produces a bioelectric neuromodulation effect in the target region, and wherein the second-polarity electrical charge injected to the neuromodulation site avoids counteracting the bioelectric neuromodulation effect.

18. The method of claim 16, wherein the first-polarity electrical charge injected to the target region in the first phase produces a first bioelectric neuromodulation effect in the target region, and wherein the second-polarity electrical charge injected to the neuromodulation site causes a second bioelectric neuromodulation effect outside of the target region.

19. The method of claim 16, wherein the first phase and the second phase are each produced using a plurality of anodes and a plurality of cathodes of the electrode arrangement, and wherein each anode used to produce the first phase is used as a cathode to produce the second phase, and each cathode used to produce the first phase is used as an anode to produce the second phase.

20. The method of claim 19, wherein, through each individual electrode, a first quantity of charge of the first polarity is injected to the neuromodulation site during the first phase and a second quantity of charge of the second polarity is injected to the neuromodulation site during the second phase, wherein the first quantity equals the second quantity.

* * * * *